United States Patent
Andrews et al.

(10) Patent No.: US 6,191,150 B1
(45) Date of Patent: Feb. 20, 2001

(54) FORMAMIDE COMPOUNDS AS THERAPEUTIC AGENTS

(75) Inventors: Robert Carl Andrews, Durham; Marc Werner Andersen, Raleigh; Dulce Garrido Bubacz, Cary; Joseph Howing Chan, Chapel Hill; David John Cowan, Hillsborough; Michael David Gaul, Apex; Daryl Lynn McDougald, Durham; David Lee Musso, Raleigh; Michael Howard Rabinowitz, Durham; Jennifer Badiang Stanford, Cary; Robert William Wiethe, Durham, all of NC (US)

(73) Assignee: Glaxo Wellcome Inc., Research Triangle Park, NC (US)

( * ) Notice: Under 35 U.S.C. 154(b), the term of this patent shall be extended for 0 days.

(21) Appl. No.: 09/382,747

(22) Filed: Aug. 25, 1999

Related U.S. Application Data

(60) Provisional application No. 60/097,959, filed on Aug. 26, 1998.

(30) Foreign Application Priority Data

Aug. 26, 1998 (GB) .................................... 9818605

(51) Int. Cl.$^7$ .................. A61K 31/44; A61K 31/425; A61K 31/38; A61K 31/215; C07D 211/72
(52) U.S. Cl. .................. 514/352; 514/371; 514/447; 514/507; 546/308; 548/195; 549/69; 562/621
(58) Field of Search .................. 548/198, 195; 514/371, 352, 447, 507; 546/308; 549/69; 562/621

(56) References Cited

U.S. PATENT DOCUMENTS

| | | |
|---|---|---|
| 4,996,358 | 2/1991 | Handa et al. . |
| 5,239,078 | 8/1993 | Galardy et al. . |
| 5,691,382 | 11/1997 | Crimmin et al. . |
| 5,747,514 | 5/1998 | Beckett et al. . |

FOREIGN PATENT DOCUMENTS

| | | |
|---|---|---|
| 0 082 088 A1 | 12/1982 | (EP) . |
| 0 236 872 A2 | 2/1987 | (EP) . |
| 92/09556 | 6/1992 | (WO) . |
| 92/09563 | 6/1992 | (WO) . |
| 93/00327 | 1/1993 | (WO) . |
| 93/13741 | 7/1993 | (WO) . |
| 93/21942 | 11/1993 | (WO) . |
| 94/07527 | 4/1994 | (WO) . |
| WO 9407527 * | 4/1994 | (WO) . |
| 94/10990 | 5/1994 | (WO) . |
| 94/22309 | 10/1994 | (WO) . |
| 95/04735 | 2/1995 | (WO) . |
| 95/06031 | 3/1995 | (WO) . |
| 95/12603 | 5/1995 | (WO) . |
| 95/19956 | 7/1995 | (WO) . |
| 95/19965 | 7/1995 | (WO) . |
| 95/22966 | 8/1995 | (WO) . |
| 95/32944 | 12/1995 | (WO) . |
| 95/33709 | 12/1995 | (WO) . |
| 96/16027 | 5/1996 | (WO) . |
| 96/20918 | 7/1996 | (WO) . |
| 97/03783 | 2/1997 | (WO) . |
| 97/19053 | 5/1997 | (WO) . |
| 98/17643 | 4/1998 | (WO) . |

OTHER PUBLICATIONS

Akiyama, M. Et al., "N–Hydroxy Amides, Part 5.+Synthesis and Properties of N–Hydroxypeptides having Leucine Enkephalin Sequences", Journ. Chem Soc., Perkin Trans. 1, (1986) pp. 851–855.

Akiyama, M. et al., "synthesis and Properties of Enkephalin Analogues Containing An N–Hydroxyamino Acid", Pept. Chem. (1985) 22:271–6.

Berner, I., et al., "Chiral Linear Hydroxamates as Biomimetic Analoguesof ferrioxamine and coprogen and their use in probing siderophore–receptor specifity in bacteria and fungi", Biol. Met. (1991)4(3): 186–91.

Devlin, J., et al., "Studies Concerning the Antibiotic Actinionin. Part III. Synthesis of Structrural analogues of actinonin by the Anhydride–Imide Method" J. Chem Soc. Perkin Trans. 1 (1975) 9:857–860.

Castelhano, et al., Chemical Abstracts, vol. 125, Abst. 143320.

Zaluski, et al., "New Bidentates as Full Inhibitors of Enkephalin–Degrading Enzymes: Synthesis and Analgesic Properties", J. Med. Chem Soc. Perkin 1 (1975) 9:830–41.

Floyd, et al., Chemical Abstracts, vol. 126, Abst. 212449.

* cited by examiner

*Primary Examiner*—Zinna Northington Davis
*Assistant Examiner*—Binta Robinson
(74) *Attorney, Agent, or Firm*—John L. Lemanowicz

(57) ABSTRACT

A family of compounds having the general structural formula

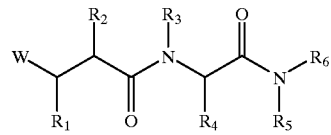

where W is a reverse hydroxamic acid group, and $R_1$, $R_2$, $R_3$, $R_4$, $R_5$ and $R_6$ are as described in the specification, or a pharmaceutically acceptable salt, solvate, biohydrolyzable ester, biohydrolyzable amide, affinity reagent, or prodrug thereof.

19 Claims, No Drawings

FORMAMIDE COMPOUNDS AS THERAPEUTIC AGENTS

This application claims priority from U.S. Provisional Application Ser. No. 60/097,959 filed Aug. 26, 1998, and GB9818605.9 also filed Aug. 26, 1998.

FIELD OF THE INVENTION

The present invention provides novel compounds, novel compositions, methods of their use and methods of their manufacture, such compounds generally pharmacologically useful as agents in those disease states alleviated by the inhibition or antagonism of matrix metalloproteases, metalloproteases, and/or tumor necrosis factor-alpha (TNF), which pathologically involve aberrant extracellular matrix degradation, shedding of cell surface protein ectodomains, and/or TNF synthesis, such disease states including arthritis, tumor metastasis and diabetes. The aforementioned pharmacologic activities are useful in the treatment of mammals.

More specifically, the compounds of the present invention can be used in the treatment of rheumatoid arthritis, osteoarthritis, inflammatory bowel syndromes, periodontal disease, aberrant angiogenesis, tumor invasion and metastasis, corneal ulceration and the complications of diabetes. At the present time, there is a need in the areas of rheumatology, oncology, dentistry, opththalmology, gastroenterology, cardiology, neurology, nephrology, infectious disease and endocrinology therapy for such agents.

BACKGROUND OF THE INVENTION

The matrix metalloprotease (MMP) family of zinc endoproteases includes fibroblast collagenase (MMP-1, collagenase-1), neutrophil collagenase (MMP-8, collagenase-2), chondrocyte collagenase (MMP-13, collagenase-3), gelatinases A and B (MMP's 2 and 9), and members of the stromelysin family such as stromelysin-1 (MMP-3), stromelysin-3 (MMP-11), and matrilysin (MMP-7). These enzymes accelerate breakdown of connective tissue by catalyzed resorption of the extracellular matrix. This is a feature of diverse pathologies; therefore, inhibitors of one or more of the matrix metalloproteases would have utility in a wide range of disease states such as in abrogating the initiation of tumor metastasis and angiogenesis and in halting the pathogenesis of demyelinating diseases of the nervous system, multiple sclerosis being one example. MMP inhibitors would also find utility in diseases involving connective tissue degradation in the joint, as occurs in osteoarthritis and rheumatoid arthritis. MMP's-1 and -3 have been found in elevated levels in the synovial fluid of patients with rheumatoid arthritis and osteoarthritis.

Collagenase-3 (MMP-13) is a member of the family of MMP's which preferentially digest collagen. Collagenase-3 is one of the more newly characterized MMP's; biochemical studies on the recombinant protein have demonstrated that it cleaves type II collagen, the predominant matrix component of articular cartilage, more efficiently than either MMP-1 or MMP-2 and that it is expressed by chondrocytes in osteoarthritic cartilage. These data would implicate collagenase-3 as a significant target in rheumatoid arthritis and osteoarthritis for inhibition by MMP inhibitors.

Compounds which inhibit the activities of one or more of the matrix metalloproteases are recognized as having therapeutic benefit in one or more pathologies where MMP activity is upregulated, such as:

i) inflammatory/autoimmune diseases, including but not limited to rheumatoid arthritis, osteoarthritis, Crohn's disease and other inflammatory bowel diseases, periodontal disease, gingivitis, and corneal ulceration;

ii) cardiovascular diseases, including but not limited to atherosclerosis and restenosis;

iii) metabolic diseases, including but not limited to complications of diabetes, osteoporosis, and other disorders involving resorption of bone;

iv) neurologic diseases, including but not limited to multiple sclerosis and other demyelination ailments;

v) diseases of cancer and malignancy, including but not limited to cancers of the oral cavity and pharynx (lip, tongue, mouth, pharynx), esophagus, stomach, small intestine, large intestine, rectum, liver and biliary passages, pancreas, larynx, lung, bone, connective tissue, skin, colon, breast, cervix uteri, corpus endometrium, ovary, prostate, testis, bladder, kidney and other urinary tissues, eye, brain and central nervous system, thyroid and other endocrine gland, leukemias (lymphocytic, granulocytic, monocytic), Hodgkin's disease, non-Hodgkin's lymphomas, multiple myeloma, tumor invasion, and metastatic and angiogenic events thereof;

vi) renal diseases, including but not limited to nephrotic syndromes and glomerulonephritis; and vii) infectious diseases, including but not limited to those mediated by viruses, bacteria, and fungi;

viii) respiratory diseases, including but not limited to emphysema and COPD.

Many inhibitors of matrix metalloproteases have been disclosed, including some structure activity relationships for a series of carboxylalkylamine inhibitors. These molecules are exemplary for MMP inhibitors in general. They generally embody a functional group capable of tightly binding the zinc cofactor at the enzyme active site, which is contained within a peptidic or pseudopeptide structure. Zinc binding groups among the MMP inhibitor art have included hydroxamic acid, reverse hydroxamic acid, thiol, carboxylate, and phosphinate.

Hydroxamate metalloprotease inhibitors disclosed in the art usually have the following general structure (I):

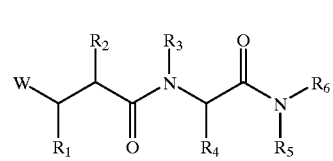

(I)

where W is a zinc-chelating acyl derivative group of the formula —C(O)NHOH (which by convention and in this application are referred to as "forward hydroxamates") or a zinc-chelating substituted amine group of the formula —NH(OH)C(O)R (which by convention and in this application are referred to as "reverse hydroxamates"), where R is usually hydrogen or alkyl. The other substituents vary according to specifications expressed by the art disclosure. It is understood and demonstrated that variations in these substituents can have dramatic effects on potency and selectivities between the matrix metalloproteases.

Suppression of MMP activity in conditions characterized by its overproduction would be of benefit, and compounds which inhibit MMP's would act in this manner at a specific target and be useful and of benefit. The present invention fills this need by providing potent, specific, orally or parenterally active inhibitors of matrix metalloproteases.

Tumor necrosis factor-α (TNFα), hereinafter called "TNF", is a mammalian protein capable of inducing cellular effects by virtue of its interaction with specific cellular receptors. It was initially characterized and so named due to its ability to cause death of cancerous cells. It is produced primarily by activated monocytes and macrophages. Human TNF is produced as a larger pro-form of 26 kD which is processed to a secreted 17 kD mature form by proteolytic processing of the alanine-76—valine-77 peptide bond.

Recently, certain compounds having matrix metalloprotease—inhibiting activity have been found to inhibit the release of mature 17 kD TNF from cells. Further, these inhibitors also protect mice from a lethal dose of endotoxin indicating that the compounds can inhibit TNF secretion in vivo. These compounds inhibit the cell-associated proteolytic processing of the 26 kD pro-TNF to the mature 17 kD form. The proteolytic activity is thought to reside in an intracellular or cell-associated specific enzyme or family of enzymes, which by convention is called a "TNF convertase", distinct from the matrix metalloproteases but related in that both contain a zinc cation at the active site. TNF convertase enzymatic activity can be detected in monocyte membrane fractions, and the enzyme activity can be inhibited by certain matrix metalloprotease—inhibiting compounds.

A metalloprotease is thought to mediate the proteolysis of the cell—surface IgE receptor CD23. Certain of the CD23—derived peptides possess proinflammatory biological activities mimicking those of cytokines, including TNFα.

Metalloprotease—like activity is also thought to contribute to the shedding of certain cell surface protein ectodomains such as L-selectin, fibronectin, thyrotropin stimulating hormone receptor, transforming growth factor alpha precursor, low density lipoprotein receptor, beta amyloid precursor protein, interleukin-6 receptor alpha subunit, Fas ligand, CD40 ligand, epidermal growth factor receptor, macrophage colony stimulating factor, interleukin-1 receptor type II, CD30, and tumor necrosis factor receptors type I and II.

TNF is known to mediate many biological responses in vivo. Preclinical and clinical studies in animals and humans with specific TNF neutralizing antibodies, soluble TNF receptor constructs, and TNF detection techniques have implicated TNF as a mediator in numerous pathologies. The compounds of the present invention by virtue of their activity in inhibiting TNF production and/or their activity in preventing cell surface protein ectodomain shedding should show utility in the treatment of diverse pathologies such as;

i) inflammatory/autoimmune diseases, including but not limited to rheumatoid arthritis, osteoartritis, Crohn's disease and other inflammatory bowel diseases and inflammatory gastrointestinal diseases, and systemic lupus erythematosis;

ii) reperfusion injuries, such as those caused by an initial ischemic event;

iii) systemic inflammatory response syndromes, including but not limited to sepsis, burn injury, pancreatitis, and adult respiratory distress syndrome;

iv) allergic and dermatologic diseases, including but not limited to delayed type hypersensitivity, psoriasis, asthma, eczema, allergic rhinitis, and allergic conjunctivitis;

v) cardiovascular diseases, including but not limited to hyperlipidemia, myocardial infarction, atherosclerosis, chronic obstructive pulmonary disease, and restenosis;

vi) metabolic diseases, including but not limited to osteoporosis, obesity, and diabetes;

vii) neurologic diseases, including but not limited to Alzheimer's disease, Parkinson's disease, multiple sclerosis, aneurism, and stroke;

viii) transplant rejection, including but not limited to organ transplant rejection and graft versus host disease;

ix) diseases of cancer and malignancy, including but not limited to cancers of the oral cavity and pharynx (lip, tongue, mouth, pharynx), esophagus, stomach, small intestine, large intestine, rectum, liver and biliary passages, pancreas, larynx, lung, bone, connective tissue, skin, colon, rectum, breast, cervix uteri, corpus endometrium, ovary, prostate, testis, bladder, kidney and other urinary tissues, eye, brain and central nervous system, thyroid and other endocrine gland, leukemias (lymphocytic, granulocytic, monocytic), Hodgkin's disease, non-Hodgkin's lymphomas, multiple myeloma, tumor invasion, and metastatic and angiogenic events thereof, x) renal diseases, including but not limited to nephrotic syndromes and glomerulonephritis;

xi) cachexia and related wasting syndromes;

xii) infectious diseases, including but not limited to HIV infection and neuropathy, Epstein-Barr viral infection, herpes viral infection, malaria, meningitis, schistosomiasis, leprosy, hepatitis (which includes hepatitis A, hepatitis B, and hepatitis C), infectious arthritis, leishmaniasis, tuberculosis, Lyme disease, and viral encephalitis;

xiii) effects of disease therapy, including but not limited to cytokine therapy, chemotherapy, radiation therapy and therapies using anti-T-cell antibodies or cytotoxin-antibody conjugates; and xiv) ocular diseases, including but not limited to diabetic retinopathy and macular degeneration.

Suppression of TNF activity in conditions characterized by its overproduction would be of benefit, and compounds which inhibit TNF convertase would act in this manner at a specific target and be useful and of benefit. The present invention fulfills this need by providing potent, specific, orally or parenterally active inhibitors of matrix metalloproteases, including potent, specific, orally or parenterally active inhibitors of TNF-alpha release from monocyte cells acting via inhibition of TNF-alpha converting enzyme (TNFc).

Suppression of shedding of cell surface protein ectodomains in conditions characterized by an overactivity of such a shedding enzyme or enzymes would be of benefit, and compounds which inhibit this cell surface protein ectodomain shedding would be useful and of benefit. The present invention fulfills this need by providing potent, orally or parenterally active inhibitors of shedding of cell surface protein ectodomains acting via inhibition of one or more specific enzymes which mediate this proteolytic event.

Furthermore, as described above, suppression of CD23 proteolysis in conditions characterized by an overabundance of CD23 proteolytic fragments would be of benefit, and compounds which inhibit CD23 proteolysis would be useful and of benefit. The present invention fulfills this need by providing potent orally or parenterally active inhibitor of CD23 proteolysis acting via inhibition of one or more specific enzymes which mediate this proteolytic event.

SUMMARY OF THE INVENTION

Accordingly it is an object of the present invention to provide a potent, specific, orally or parenterally active inhibitor of MMP's.

It is another object of the present invention to provide a potent, specific, orally or parenterally active inhibitor of TNF-alpha release from monocyte cells acting via inhibition of TNF-alpha converting enzyme (TNFc).

A further object of the present invention to provide a potent, orally or parenterally active inhibitor of shedding of cell surface protein ectodomains acting via inhibition of one or more specific enzymes which mediate this proteolytic event.

It is yet another object of the present invention to provide a potent orally or parenterally active inhibitor of CD23 proteolysis acting via inhibition of one or more specific enzymes which mediate this proteolytic event.

It is therefore an object of the present invention to provide a compound of the formula:

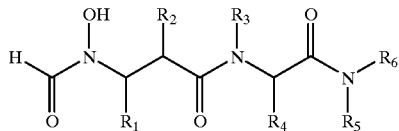
(II)

where $R_1$ is

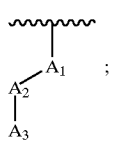

where $A_1$ is alkylene, alkenylene, alkynylene, or a direct bond;
$A_2$ is O, S, SO, $SO_2$, or a direct bond;
$A_3$ is alkyl, alkenyl, alkynyl, cycloalkyl, cycloalkenyl, heterocyclyl, heteroaryl, aryl, or hydrogen;
$R_2$ is

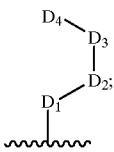

where $D_1$ is

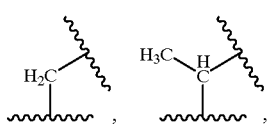

or a direct bond,
$D_2$ is alkylene, alkenylene, alkynylene, or a direct bond,
$D_3$ is cycloalkylene, cycloalkenylene, heterocyclylene, arylene, hetereroarylene, or a direct bond,
$D_4$ is alkyl, aryl, heteroaryl, or hydrogen;
$R_3$ is hydrogen or lower alkyl;

$R_4$ is

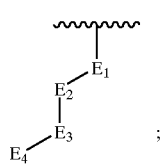

where $E_1$ is alkylene, alkenylene, alkynylene, or a direct bond,
$E_2$ is S, O, SO, $SO_2$, C(O)O, OC(O), $NR_7$, C(O)$NR_7$, $NR_7$C(O), $SO_2NR_7$, or a direct bond, where $R_7$ is as defined below;
$E_3$ is alkylene, cycloalkylene, cycloalkenylene, arylene, heterocyclylene, heteroarylene, or a direct bond;
$E_4$ is

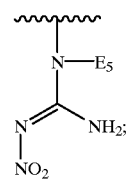

$E_5$ is lower alkyl or hydrogen;
$R_5$ is hydrogen or lower alkyl;
$R_6$ is

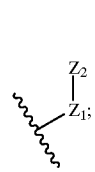

where $Z_1$ is heteroarylene or a direct bond;
$Z_2$ is alkyl, alkenyl, alkynyl, cycloalkyl, cycloalkenyl, heterocyclyl, heteroaryl, aryl, $NR_8R_9$, $OR_8$, or hydrogen, where $R_8$ and $R_9$ are as defined below; and
$R_7$, $R_8$, and $R_9$ are, independently, hydrogen, alkyl, alkynyl, alkenyl, cycloalkyl, cycloalkenyl, aryl, heterocyclyl, or heteroaryl;

or a pharmaceutically acceptable salt, solvate, biohydrolyzable ester, biohydrolyzable amide, affinity reagent, or prodrug thereof.

DETAILED DESCRIPTION OF THE INVENTION

The present invention provides a family of compounds having the general structural formula:

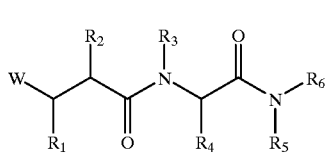
(I)

or a pharmaceutically acceptable salt, solvate, biohydrolyzable esters, biohydrolyzable amides, affinity reagents, or prodrugs thereof, wherein W is a reverse hydroxamic acid group;
  $R_1$ is a substituent other than hydrogen;
  $R_4$ is a lipophilic substituent containing a nitro—substituted guanidine group, and;
  $R_6$ is hydrogen, or an alkyl or heteroaryl substituent.

Such compounds are novel and are unknown in the art and, given the appropriate choice of $R_1$, $R_2$, $R_3$, $R_4$, $R_5$, and $R_6$ as described herein, show potent inhibition of MMP's, cell-free TNF convertase enzyme and TNF release from cells, and in some cases inhibit TNF convertase and TNF release from cells in preference to matrix metalloproteases. The selection of $R_6$ as heteroaryl in combination with an appropriate choice of $R_1$, $R_2$, $R_3$, $R_4$, and $R_5$ as described hereinis beneficial in achieving increased potency against TNF release from cells relative to inhibition of MMP's. Such molecules can be selective for TNF inhibition over MMP's and can possess an improved therapeutic profile where inhibition of one or more of the matrix metalloproteases is associated with an adverse biological response or abnormal pathology. An appropriate choice of $R_1$, $R_2$, $R_3$, $R_4$, $R_5$, and $R_6$ as described herein is also beneficial in achieving selective inhibition of one or more of the matrix metalloproteases (for example, collagenase-3) in preference to TNF convertase inhibition and inhibition of TNF release from whole cells.

In particular, reverse hydroxamate compounds of the present invention include those of the formula (II):

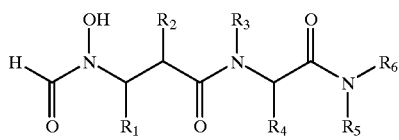

(II)

where
  $R_1$ is

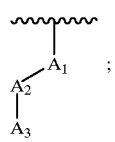

where
  $A_1$ is alkylene, alkenylene, alkynylene, or a direct bond;
  $A_2$ is O, S, SO, $SO_2$, or a direct bond;
  $A_3$ is alkyl, alkenyl, alkynyl, cycloalkyl, cycloalkenyl, heterocyclyl, heteroaryl, aryl, or hydrogen;
  $R_2$ is

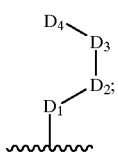

where
  $D_1$ is

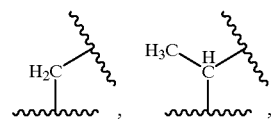

or a direct bond,
  $D_2$ is alkylene, alkenylene, alkynylene, or a direct bond,
  $D_3$ is cycloalkylene, cycloalkenylene, heterocyclylene, arylene, hetereroarylene, or a direct bond,
  $D_4$ is alkyl, aryl, heteroaryl, or hydrogen;
  $R_3$ is hydrogen or lower alkyl;
  $R_4$ is

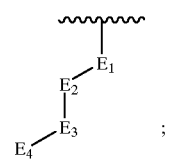

where
  $E_1$ is alkylene, alkenylene, alkynylene, or a direct bond,
  $E_2$ is S, O, SO, $SO_2$, C(O)O, OC(O), $NR_7$, $C(O)NR_7$, $NR_7C(O)$, $SO_2NR_7$, or a direct bond, where $R_7$ is as defined below;
  $E_3$ is alkyene, cycloalkylene, cycloalkenylene, arylene, heterocyclylene, heteroarylene, or a direct bond;
  $E_4$ is

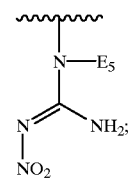

$E_5$ is lower alky or hydrogen;
  $R_5$ is hydrogen or lower alkyl;
  $R_6$ is

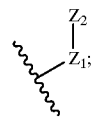

where
  $Z_1$ is heteroarylene or a direct bond;
  $Z_2$ is alkyl, alkenyl, alkynyl, cycloalkyl, cycloalkenyl, heterocyclyl, heteroaryl, aryl, $NR_8R_9$, $OR_8$, or hydrogen, where $R_8$ and $R_9$ are as defined below;
  $R_7$, $R_8$, and $R_9$ are, independently, hydrogen, alkyl, alkynyl, alkenyl, cycloalkyl, cycloalkenyl, aryl, heterocyclyl, or heteroaryl;
or a pharmaceutically acceptable salt, solvate, biohydrolyzable ester, biohydrolyzable amide, affinity reagent, or prodrug thereof.

Compounds of the present invention which are currently preferred for their high biological activity are listed below in Table 1; variables below are with reference to the generic structure (I).

TABLE I
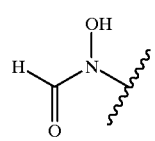
(I)
| Example | W | R₁ | R₂ | R₃ | R₄ | R₅ | R₆ |
|---------|---|----|----|----|----|----|----|
| 1 | 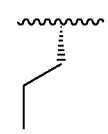 | 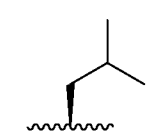 | 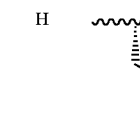 | H | 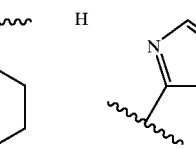 | H | 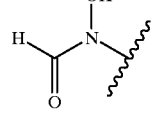 |
| 2 | 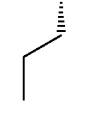 | 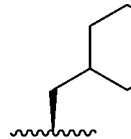 | 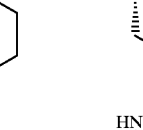 | H | 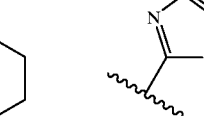 | H | 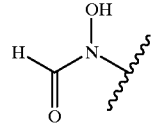 |
| 3 |  | 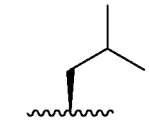 | 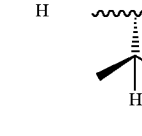 | H | 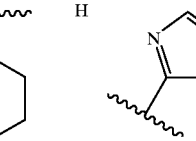 | H | 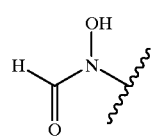 |
| 4 | 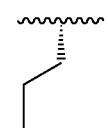 | 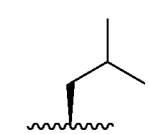 | 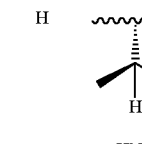 | H | 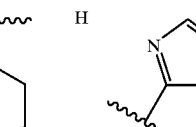 | H | 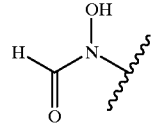 |

TABLE I-continued
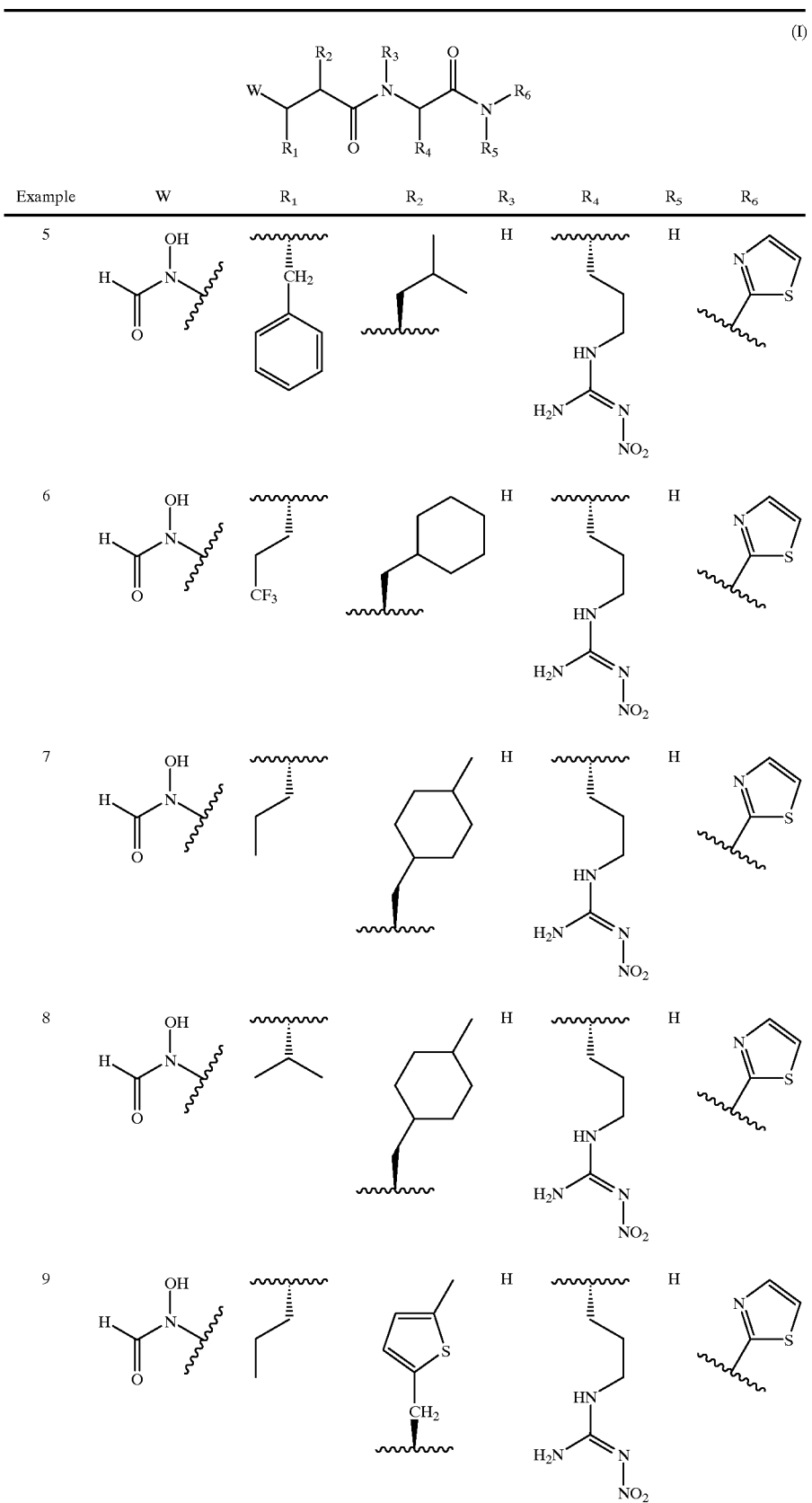

TABLE I-continued (I)

| Example | W | R₁ | R₂ | R₃ | R₄ | R₅ | R₆ |
|---------|---|----|----|----|----|----|-----|
| 10 | N(OH)CHO | cyclopropyl | CH₂-cyclohexyl | H | (CH₂)₃NHC(=NNO₂)NH₂ | H | 2-thiazolyl |
| 11 | N(OH)CHO | n-propyl | CH₂-phenyl | H | (CH₂)₃NHC(=NNO₂)NH₂ | H | 2-thiazolyl |
| 12 | N(OH)CHO | n-propyl | CH₂-phenyl | H | (CH₂)₃NHC(=NNO₂)NH₂ | H | CH₃ |
| 13 | N(OH)CHO | n-propyl | CH₂-phenyl | H | (CH₂)₃NHC(=NNO₂)NH₂ | H | H |
| 14 | N(OH)CHO | H | (CH₂)₂-phenyl | H | (CH₂)₃NHC(=NNO₂)NH₂ | H | CH₃ |

TABLE I-continued (I)

| Example | W | R₁ | R₂ | R₃ | R₄ | R₅ | R₆ |
|---------|---|----|----|----|----|----|----|
| 15 | N(OH)CHO | H | CH₂CH₂-phenyl | H | (CH₂)₃NHC(=NNO₂)NH₂ | H | thiazol-2-yl |
| 16 | N(OH)CHO | CF₃ | CH₂-(4-methylcyclohexyl) | H | (CH₂)₃NHC(=NNO₂)NH₂ | H | thiazol-2-yl |
| 17 | N(OH)CHO | CF₃ | CH₂CH₂-phenyl | H | (CH₂)₃NHC(=NNO₂)NH₂ | H | thiazol-2-yl |
| 18 | N(OH)CHO | CF₃ | CH₂CH₂-phenyl | H | (CH₂)₃NHC(=NNO₂)NH₂ | H | H |
| 19 | N(OH)CHO | CF₃ | CH₂CH₂-phenyl | H | (CH₂)₃NHC(=NNO₂)NH₂ | H | CH₃ |

TABLE I-continued

Compounds of the present invention which are currently preferred for their biological are listed by name below in Table 2.

TABLE 2

| Example | Chemical Name |
|---|---|
| 1 | (2R,3S)-3-(Formyl-hydroxyamino)-2-(2-methyl-1-propyl) hexanoic Acid [(1S)-4-(nitroimino-amino)methylamino-1-(1,3-thiazol-2-ylcarbamoyl)-1-butyl]amide |
| 2 | (2R,3S-3-(Formyl-hydroxyamino)-2-(cyclohexylmethyl)hexanoic Acid [(1S)-4-(nitroimino-amino)methylamino-1-(1,3-thiazol-2-ylcarbamoyl)-1-butyl]amide |
| 3 | (2R,3S)-3-(Formyl-hydroxyamino)-2-(2-methyl-1-propyl) butanoic Acid [(1S,2R)-2-Methyl-4-(nitroimino-amino) methylamino-1-(1,3-thiazol-2-ylcarbamoyl)-1-butyl]amide |
| 4 | (2R,3S)-3-(Formyl-hydroxyamino)-2-(2-methyl-1-propyl) hexanoic Acid [(1S,2R)-2-Methyl-4-(nitroimino-amino) methylamino-1-(1,3-thiazol-2-ylcarbamoyl)-1-butyl]amide |
| 5 | (2R,3S-3-(Formyl-hydroxyamino)-2-(2-methyl-1-propyl)-4-phenylbutanoic Acid [(1S)-4-(nitroimino-amino)methylamino-1-(1,3-thiazol-2-ylcarbamoyl)-1-butyl]amide |

TABLE 2-continued

| Example | Chemical Name |
|---|---|
| 6 | (2R,3S)-3-(Formyl-hydroxyamino)-2-(cyclohexylmethyl)-6,6,6-trifluorohexanoic Acid [(1S)-4-(nitroimino-amino) methylamino-1-(1,3-thiazol-2-ylcarbamoyl)-1-butyl]amide |
| 7 | (2R,3S)-3-(Formyl-hydroxyamino)-2-(4-methylcyclohexyl-methyl)hexanoic Acid [(1S)-4-(nitroimino-amino)methyl-amino-1-(1,3-thiazol-2-ylcarbamoyl)-1-butyl]amide |
| 8 | (2R,3S)-3-(Formyl-hydroxyamino)-2-(4-methylcyclohexyl-methyl)-4-methylpentanoic Acid [(1S)-4-(nitroimino-amino) methylamino-1-(1,3-thiazol-2-ylcarbamoyl)-1-butyl]amide |
| 9 | (2R,3S)-3-(Formyl-hydroxyamino)-2-(5-methyl-2-thio-phenemethyl)hexanoic Acid [(1S)-4-((nitroimino-amino) methylamino)-1-(1,3-thiazol-2-ylcarbamoyl)-1-butyl]amide |
| 10 | (2R,3S)-3-(Formyl-hydroxyamino)-2-(cyclohexylmethyl)-3-cyclopropylpropanoic Acid [(1S)-4-(nitroimino-amino) methylamino-1-(1,3-thiazol-2-ylcarbamoyl)-1-butyl]amide |
| 11 | (2R,3S)-3-(Formyl-hydroxyamino)-2-benzylhexanoic Acid [(1S)-4-(nitroimino-amino)methylamino-1-(1,3-thiazol-2-ylcarbamoyl)-1-butyl]amide |

TABLE 2-continued

| Example | Chemical Name |
|---|---|
| 12 | (2R,3S)-3-(Formyl-hydroxyamino)-2-benzylhexanoic Acid [(1S)-4-(nitroimino-amino)methylamino-1-methylcarbamoyl-1-butyl]amide |
| 13 | (2R,3S)-3-(Formyl-hydroxyamino)-2-benzylhexanoic Acid [(1S)-4-(nitroimino-amino)methylamino-1-carbamoyl-1-butyl]amide |
| 14 | (2R,3S)-3-(Formyl-hydroxyamino)-2-(3-phenyl-1-propyl)butanoic Acid [(1S)-4-(nitroimino-amino)methylamino-1-methylcarbamoyl-1-butyl]amide |
| 15 | (2R,3S)-3-(Formyl-hydroxyamino)-2-(3-phenyl-1-propyl)butanoic Acid [(1S)-4-(nitroimino-amino)methylamino-1-(1,3-thiazol-2-ylcarbamoyl)-1-butyl]amide |
| 16 | (2R,3S)-3-(Formyl-hydroxyamino)-2-(3-phenyl-1-propyl)-6,6,6-trifluorohexanoic Acid [(1S)-4-(nitroimino-amino)methylamino-1-(1,3-thiazol-2-ylcarbamoyl)-1-butyl]amide |
| 17 | (2R,3S)-3-(Formyl-hydroxyamino)-2-(3-phenyl-1-propyl)-6,6,6-trifluorohexanoic Acid [(1S)-4-(nitroimino-amino)methylamino-1-(1,3-thiazol-2-ylcarbamoyl)-1-butyl]amide |
| 18 | (2R,3S)-3-(Formyl-hydroxyamino)-2-(3-phenyl-1-propyl)-6,6,6-trifluorohexanoic Acid [(1S)-4-(nitroimino-amino)methylamino-1-carbamoyl-1-butyl]amide |
| 19 | (2R,3S)-3-(Formyl-hydroxyamino)-2-(3-phenyl-1-propyl)-6,6,6-trifluorohexanoic Acid [(1S)-4-(nitroimino-amino)methylamino-1-methylcarbamoyl-1-butyl]amide |
| 20 | (2R,3S)-3-(Formyl-hydroxyamino)-2-(2-methyl-1-propyl)-6,6,6-trifluorohexanoic Acid [(1S)-4-(nitroimino-amino)methylamino-1-(1,3-thiazol-2-ylcarbamoyl)-1-butyl]amide |
| 21 | (2R,3S)-3-(Formyl-hydroxyamino)-2-(2-methyl-1-propyl)-6,6,6-trifluorohexanoic Acid [(1S)-4-(nitroimino-amino)methylamino-1-carbamoyl-1-butyl]amide |
| 22 | (2R,3S)-3-(Formyl-hydroxyamino)-2-(2-methyl-1-propyl)-6,6,6-trifluorohexanoic Acid [(1S)-4-(nitroimino-amino)methylamino-1-methylcarbamoyl-1-butyl]amide |

Preferred embodiments of the invention include compounds of general formula (II) where $R_1$ is methyl, trifluoromethyl, ethyl, phenylsulfanylmethyl, phenylsulfonylmethyl, thiophene-2-sulfanylmethyl, thiophene-2-sulfonylmethyl, isopropyl, 3-methyl-1-butyl, benzylmethyl, 2-benzyloxy-1-ethyl, benzyl, n-propyl, 3,3,3-trifluoro-1-propyl, or cycloprpyl;

$R_2$ is isobutyl, cyclohexylmethyl, 3-(2-furyl)-1-propyl, 3-(4-biphenyl)-1-propyl, 4-methylcycohexylmethyl, cycloheptylmethyl, cyclohexyl, 5-methylthiophene-2-methyl, 4-phenyl-1-butyl, 3-phenyl-1-propyl, or benzyl;

$R_3$ is hydrogen, methyl, or ethyl;

$R_4$ is 3-(nitroimino-amino)methylamino-1-propyl, 3-(nitroimino-amino)methyl-ethlamino-1-propyl, 3-(nitroimino-amino)methyl-methylamino-1-propyl, 3-(nitroiminohyl-amino)methyl-isopropylamino-1-propyl, 2-(nitroimino-amino)methylamino-1-ethylaminocarbonylethyl, 2-(nitroimino-amino)methylamino-1-ethylaminocarbonylmethyl, 4-(nitroimino-amino)methylamino-1-butyl, or 4-(nitroimino-amino)methylamino-2-butyl;

$R_5$ is hydrogen, methyl, ethyl, or n-propyl; and $R_6$ is hydrogen, methyl, 5-ethyl-2-thiazolyl, cyclopropyl, cyclobutyl, cycloheptyl, 2,2,2-trifluoroethyl, cyclopentyl, 3-cyclopenten-1-yl, 2-pyridyl, 1,3,4-thiadiazol-2-yl, or 2-thiazolyl.

Particularly preferred embodiments of the invention include compounds of general formula (II) where $R_1$ is methyl, isopropyl, benzyl, n-propyl, 3,3,3-trifluoro-1-propyl, or cyclopropyl;

$R_2$ is isobutyl, cyclohexylmethyl, 4-methylcyclohexylmethyl, 5-methylthiophene-2-methyl, 3-phenyl-1-propyl, or benzyl;

$R_3$ is hydrogen;

$R_4$ is 3-(nitroimino-amino)methylamino-1-propyl, or 4-(nitroimino-amino)methylamino-2-butyl;

$R_5$ is hydrogen; and $R_6$ is hydrogen, methyl, or 2-thiazolyl.

More particularly preferred embodiments of the invention include compounds of general formula (II) where $R_1$ is methyl, n-propyl, or 3,3,3-trifluoro-1-propyl;

$R_2$ is isobutyl, 3-phenyl-1-propyl, or benzyl;

$R_3$ is hydrogen;

$R_4$ is 3-(nitroimino-amino)methylamino-1-propyl;

$R_5$ is hydrogen; and $R_6$ is hydrogen, methyl, or 2-thiazolyl.

The compounds of the present invention are inhibitors of matrix metalloproteases, TNF converting enzyme, and TNF activity from whole cells. The compounds of the present invention may also inhibit shedding of pathologically significant cell surface protein ectodomains. The compounds of the present invention may also inhibit proteolysis of CD23. The invention described herein is additionally directed to pharmaceutical compositions and methods of inhibiting matrix metalloprotease and/or TNF activity and/or CD23 proteolytic fragment activity in a mammal, which methods comprise administering to a mammal in need of a therapeutically defined amount of a compound of formula (I) or (II), defined above, as a single or polymorphic crystalline form or forms, an amorphous form, a single enantiomer, a racemic mixture, a single stereoisomer, a mixture of stereoisomers, a single diastereoisomer, a mixture of diastereomers, a solvate, a pharmaceutically acceptable salt, a solvate, a prodrug, a biohydrolyzable ester, or a biohydrolyzable amide thereof.

According to a further aspect of the present invention there is provided a compound of formula (II) as defined above or a pharmaceutically acceptable salt, solvate, biohydrolyzable ester, biohydrolyzable amide, affinity reagent, or prodrug thereof for use in therapy.

Thus, the present invention provides a method of inhibiting a matrix metalloprotease, comprising the step of administering to a mammal in need thereof a pharmacologically effective amount of a compound of the present invention. The invention further provides a pharmaceutical composition comprising a pharmaceutically acceptable carrier and a pharmacologically effective amount of a compound of the present invention sufficient to inhibit a matrix metalloprotease. A matrix metalloprotease-inhibiting amount can be an amount that reduces or inhibits a matrix metalloprotease activity in the subject.

According to a further aspect of the present invention there is also provided the use of a compound of formula (II) as defined above or a pharmaceutically acceptable salt, solvate, biohydrolyzable ester, biohydrolyzable amide, affinity reagent, or prodrug thereof in the preparation of a medicament for inhibiting a matrix metalloprotease.

The present invention further provides a method of inhibiting the intracellular release of tumor necrosis factor alpha, comprising the step of administering to a mammal in need thereof a pharmacologically effective amount of a compound of the present invention. The invention further provides a pharmaceutical composition comprising a pharmaceutically acceptable carrier and a pharmacologically effective amount of a compound of the present invention sufficient to inhibit cellular release of mature tumor necrosis factor. An amount sufficient to inhibit cellular release of mature tumor necrosis factor can be an amount that reduces or inhibits cellular release of mature tumor necrosis factor in the subject.

According to a further aspect of the present invention there is also provided the use of a compound of formula (II) as defined above or a pharmaceutically acceptable salt, solvate, biohydrolyzable ester, biohydrolyzable amide, affinity reagent, or prodrug thereof in the preparation of a medicament for inhibiting the intracellular release of tumor necrosis factor alpha.

Also provided is a method of inhibition of shedding of cell surface protein ectodomains, comprising the step of administering to a mammal in need thereof a pharmacologically effective amount of a compound of the present invention. The invention further provides a pharmaceutical composition comprising a pharmaceutically acceptable carrier and a pharmacologically effective amount of a compound of the present invention sufficient to inhibit shedding of cell surface protein ectodomains. An amount sufficient to inhibit shedding of cell surface protein ectodomains can be an amount that reduces or inhibits shedding of one or more cell surface protein ectodomains, such as L-selectin, fibronectin, thyrotropin stimulating hormone receptor, transforming growth factor alpha precursor, low density lipoprotein receptor, beta amyloid precursor protein, interleukin-6 receptor alpha subunit, Fas ligand, CD40 ligand, epidermal growth factor receptor, macrophage colony stimulating factor, interleukin-1 receptor type II, CD30, and tumor necrosis factor receptors type I and II, in the subject.

According to a further aspect of the present invention there is also provided the use of a compound of formula (II) as defined above or a pharmaceutically acceptable salt, solvate, biobydrolyzable ester, biohydrolyzable amide, affinity reagent, or prodrug thereof in the preparation of a medicament for inhibiting the shedding of cell surface protein ectodomains.

Also provided is a method of inhibiting CD23 proteolysis, comprising the step of administering to a mammal in need thereof a pharmacologically effective amount of a compound of the present invention. The invention further provides a pharmaceutical composition comprising a pharmaceutically acceptable carrier and a pharmacologically effective amount of a compound of the present invention sufficient to inhibit CD23 proteolysis. An amount sufficient to inhibit CD23 proteolysis can be an amount that reduces or inhibits CD23 proteolysis in the subject.

According to a further aspect of the present invention there is also provided the use of a compound of formula (II) as defined above or a pharmaceutically acceptable salt, solvate, biohydrolyzable ester, biohydrolyzable amide, affinity reagent, or prodrug thereof in the preparation of a medicament for inhibiting CD23 proteolysis.

Additionally provided is a pharmaceutical composition comprising a pharmaceutically acceptable carrier and a pharmacologically effective amount of a compound of the present invention sufficient to decrease, or inhibit, a malignant growth.

According to a further aspect of the present invention there is also provided the use of a compound of formula (II) as defined above or a pharmaceutically acceptable salt, solvate, biohydrolyzable ester, biohydrolyzable amide, affinity reagent, or prodrug thereof in the preparation of a medicament for inhibiting the growth of tumor metastases.

Further, the present invention provides a pharmaceutical composition comprising a pharmaceutically acceptable carrier and a pharmacologically effective amount of a compound of the present invention sufficient to treat arthritis. Such an amount can be an amount that relieves, i.e., reduces or eliminates, one or more physiologic characteristic of arthritis.

According to a further aspect of the present invention there is also provided the use of a compound of formula (II) as defined above or a pharmaceutically acceptable salt, solvate, biohydrolyzable ester, biohydrolyzable amide, affinity reagent, or prodrug thereof in the preparation of a medicament for treating arthritis.

Also provided is a pharmaceutical composition comprising a pharmaceutically acceptable carrier and a pharmacologically effective amount of a compound of the present invention sufficient to treat diabetes. Such an amount can be an amount that reduces or eliminates one or more of the complications associated with diabetes.

According to a further aspect of the present invention there is also provided the use of a compound of formula (II) as defined above or a pharmaceutically acceptable salt, solvate, biohydrolyzable ester, biohydrolyzable amide, affinity reagent, or prodrug thereof in the reparation of a medicament for treating diabetes.

Also provided is a pharmaceutical composition comprising a pharmaceutically acceptable carrier and a pharmacologically effective amount of a compound of the present invention sufficient to treat periodontal disease. Such an amount can be an amount that reduces or eliminates one or more of the complications associated with periodontal disease. According to a further aspect of the present invention there is also provided the use of a compound of formula (II) as defined above or a pharmaceutically acceptable salt, solvate, biohydrolyzable ester, biohydrolyzable amide, affinity reagent, or prodrug thereof in the preparation of a medicament for treating periodontal disease.

Additionally, the present invention contemplates treating any of these diseases/conditions in a subject by administering to the subject the recited pharmaceutical composition.

The compounds of the present invention can be administered to any mammal in need of inhibition of matrix metalloprotease activity, CD23 proteolysis, shedding of cell surface protein ectodomains and/or TNF activity. Such mammals can include, for example, horses, cows, sheep, pigs, mice, dogs, cats, primates such as chimpanzees, gorillas, rhesus monkeys, and, most preferably humans.

Certain examples of the invention also are orally or parenterally bioavailable in animals and possess oral or parenteral activity in animal models of disease.

Salts encompassed within the term "pharmaceutically acceptable salts" refer to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitaitate, Borate, Bromide, Calcium Edetate, Camsylate, Carbonate, Chloride, Clavulanate, Citrate, Dihydrochioride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate.

Other salts which are not pharmaceutically acceptable may be useful in the preparation of compounds of formula (I) or (II) and these form a further aspect of the invention.

Also included within the scope of the invention are the individual enantiomers of the compounds represented by formula (I) or (II) above as well as any wholly or partially racemic mixtures thereof. The present invention also covers the individual enantiomers of the compounds represented by formula above as mixtures with diastereoisomers thereof in which one or more of the three stereocenters are inverted.

As used herein, the term "lower" refers to a group having between one and six carbons.

As used herein, the term "alkyl" refers to a straight or branched chain hydrocarbon having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkyl" as used herein include, but are not limited to, n-butyl, n-pentyl, isobutyl, and isopropyl, and the like.

As used herein, the term "alkylene" refers to a straight or branched chain divalent hydrocarbon radical having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkylene" as used herein include, but are not limited to, methylene, ethylene, and the like.

As used herein, the term "alkenyl" refers to a hydrocarbon radical having from two to ten carbons and at least one carbon—carbon double bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed.

As used herein, the term "alkenylene" refers to an straight or branched chain divalent hydrocarbon radical having from two to ten carbon atoms and one or more carbon carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon—carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed.

As used herein, the term "alkynylene" refers to a straight or branched chain divalent hydrocarbon radical having from two to ten carbon atoms and one or more carbon—carbon triple bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkynylene" as used herein include, but are not limited to, ethyne-1,2-diyl, propyne-1,3-diyl, and the like.

As used herein, "cycloalkyl" refers to a alicyclic hydrocarbon group with one or more degrees of unsaturation, having from three to twelve carton atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to an non-aromatic alicyclic divalent hydrocarbon radical having from three to twelve carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "cycloalkenyl" refers to a substituted alicyclic hydrocarbon radical having from three to twelve carbon atoms and at least one carbon—carbon double bond in the ring system, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkenylene" as used herein include, but are not limited to, 1-cyclopentene-3-yl, 1-cyclohexene-3-yl, 1-cycloheptene-4-yl, and the like.

As used herein, the term "cycloalkenylene" refers to a substituted alicyclic divalent hydrocarbon radical having from three to twelve carbon atoms and at least one carbon—carbon double bond in the ring system, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkenylene" as used herein include, but are not limited to, 4,5-cyclopentene-1,3-diyl, 3,4-cyclohexene-1,1-diyl, and the like.

As used herein, the term "heterocyclic" or the term "heterocyclyl" refers to a three to twelve-membered heterocyclic ring having one or more degrees of unsaturation containing one or more heteroatomic substitutions selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, pyran, 1,4-dioxane, 1,3-dioxane, piperidine, pyrrolidine, morpholine, tetrahydrothiopyran, tetrahydrothiophene, and the like.

As used herein, the term "heterocyclylene" refers to a three to twelve-membered heterocyclic ring diradical having one or more degrees of unsaturation containing one or more heteroatoms selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, and the like.

As used herein, the term "aryl" refers to a benzene ring or to an optionally substituted benzene ring system fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, or lower perfluoroalkyl, multiple degrees of substitution being allowed. Examples of aryl include, but are not limited to, phenyl, 2-naphthyl, 1-naphthyl, and the like.

As used herein, the term "arylene" refers to a benzene ring diradical or to a benzene ring system diradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, or lower perfluoroalkyl, multiple degrees of substitution being allowed. Examples of "arylene" include, but are not limited to, benzene-1,4-diyl, naphthalene-1,8-diyl, anthracene-1,4-diyl, and the like.

As used herein, the term "heteroaryl" refers to a five—to seven—membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole, and the like.

As used herein, the term "heteroarylene" refers to a five—to seven—membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, or lower perfluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "direct bond", where part of a structural variable specification, refers to the direct joining of the substituents flanking (preceding and succeeding) the variable taken as a "direct bond". Where two or more consecutive variables are specified each as a "direct bond", those substituents flanking (preceding and succeeding) those two or more consecutive specified "direct bonds" are directly joined.

As used herein, the term "alkoxy" refers to the group $R_aO$—, where $R_a$ is alkyl.

As used herein, the term "alkenyloxy" refers to the group $R_aO$—, where $R_a$ is alkenyl.

As used herein, the term "alkynyloxy" refers to the group $R_aO$—, where $R_a$ is alkynyl.

As used herein, the term "alkylsulfanyl" refers to the group $R_aS$—, where $R_a$ is alkyl.

As used herein, the term "alkenylsulfanyl" refers to the group $R_aS$—, where $R_a$ is alkenyl.

As used herein, the term "alkynylsulfanyl" refers to the group $R_aS$—, where $R_a$ is alkynyl.

As used herein, the term "alkylsulfenyl" refers to the group $R_aS(O)$—, where $R_a$ is alkyl.

As used herein, the term "alkenylsulfenyl" refers to the group $R_aS(O)$—, where $R_a$ is alkenyl.

As used herein, the term "alkynylsulfenyl" refers to the group $R_aS(O)$—, where $R_a$ is alkynyl.

As used herein, the term "alkylsulfonyl" refers to the group $R_aSO_2$—, where $R_a$ is alkyl.

As used herein, the term "alkenylsulfonyl" refers to the group $R_aSO_2$—, where $R_a$ is alkenyl.

As used herein, the term "alkylsulfonyl" refers to the group $R_aSO_2$—, where $R_a$ is alkynyl.

As used herein, the term "acyl" refers to the group $R_aC(O)$—, where $R_a$ is alkyl, alkenyl, alkynyl, cycloalkyl, cycloalkenyl, or heterocyclyl.

As used herein, the term "aroyl" refers to the group $R_aC(O)$—, where $R_a$ is aryl.

As used herein, the term "heteroaroyl" refers to the group $R_aC(O)$—, where $R_a$ is heteroaryl.

As used herein, the term "alkoxycarbonyl" refers to the group $R_aOC(O)$—, where $R_a$ is alky.

As used herein, the term "acyloxy" refers to the group $R_aC(O)O$—, where $R_a$ is alkyl, alkenyl, alkynyl, cycloalkyl, cycloalkenyl, or heterocyclyl.

As used herein, the term "aroyloxy" refers to the group $R_aC(O)O$—, where $R_a$ is aryl.

As used herein, the term "heteroaroyloxy" refers to the group $R_aC(O)O$—, where $R_a$ is heteroaryl.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the terms "contain" or "containing" can refer to in-line substitutions at any position along the above-defined alkyl, alkenyl, alkynyl or cycloalkyl substituents with one or more of any of O, S, SO, $SO_2$, N, or N-alkyl, including, for example, —$CH_2$—O—$CH_2$—, —$CH_2$—$SO_2$—$CH_2$—, —$CH_2$—NH—$CH_3$ and so forth.

As used herein, the term "solvate" is a complex of variable stoichiometry formed by a solute (in this invention, a compound of formula (I) or (II)) and a solvent. Such solvents for the purpose of the invention may not interfere with the biological activity of the solute. Solvents may be, by way of example, water, ethanol, or acetic acid.

As used herein, the term "biohydrolyzable ester" is an ester of a drug substance (in this invention, a compound of general formula (I) or (II)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) or (II) in plasma. Many examples of such are known in the art and include by way of example lower alkyl esters, lower acyloxy-alkyl esters, lower alkoxyacyloxyalkyl esters, alkoxyacyloxy esters, alkyl acylamino alkyl esters, and choline esters. An example of such a biohydrolyzable ester applied to the general formula (II) is illustrated below in general formula (III).

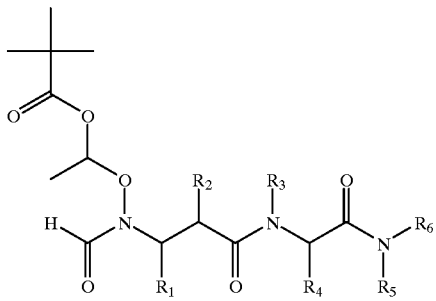

(III)

As used herein, the term "biohydrolyzable amide" is an amide of a drug substance (in this invention, a compound of general formula (I) or (II)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) or (II) in plasma. Many examples of such are known in the art and include by way of example lower alkyl amides, α-amino acid amides, alkoxyacyl amides, and alkylaminoalkylcarbonyl amides.

As used herein, the term "prodrug" includes biohydrolyzable amides and biohydrolyzable esters and also encompasses a) compounds in which the biohydrolyzable functionality in such a prodrug is encompassed in the compound of formula (I) or (II): for example, the lactam formed by a carboxylic group in $R_2$ and an amine in $R_4$, and b) compounds which may be oxidized or reduced biologically at a given functional group to yield drug substances of formula (I) or (II). Examples of these functional groups are, but are not limited to, 1,4-dihydropyridine, N-alkylcarbonyl-1,4-dihydropyridine, 1,4-cyclohexadiene, tert-butyl, and the like.

As used herein, the term "affinity reagent" is a group attached to the compound of formula (I) or (II) which does not affect its in vitro biological activity, allowing the compound to bind to a target, yet such a group binds strongly to a third component allowing a) characterization of the target as to localization within a cell or other organism component, perhaps by visualization by fluorescence or radiography, or b) facile separation of the target from an unknown mixture of targets, whether proteinaceous or not proteinaceous. An example of an affinity reagent according to b) would be biotin either directly attached to (I) or (II) or linked with a spacer of one to 50 atoms selected from the group consisting of C, H, O, N, S, or P in any combination. An example of an affinity reagent according to a) above would be fluorescein, either directly attached to (I) or (II) or linked with a spacer of one to 50 atoms selected from the group consisting of C, H, O, N, S, or P in any combination.

The term "pharmacologically effective amount" shall mean that amount of a drug or pharmaceutical agent that will elicit the biological or medical response of a tissue, system, animal or human that is being sought by a researcher or clinician. This amount can be a therapeutically effective amount.

Whenever the terms "alkyl" or "aryl" or either of their prefix roots appear in a name of a substituent (e.g. arylalkoxyaryloxy) they shall be interpreted as including those limitations given above for "alkyl" and "aryl". Alkyl or cycloalkyl substituents shall be recognized as being functionally equivalent to those having one or more degrees of unsaturation. Designated numbers of carbon atoms (e.g. $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

As used herein, the term "oxo" shall refer to the substituent=O.

As used herein, the term "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent —SO$_2$NH$_2$.

As used herein, the term "carbamoyl" shall refer to the substituent —C(O)NH$_2$.

As used herein, the term "sulfanyl" shall refer to the substituent —S—.

As used herein, the term "sulfenyl" shall refer to the substituent —SO(O)—.

As used herein, the term "sulfonyl" shall refer to the substituent —S(O)$_2$—.

The compounds of formulae (I) and (II) can be prepared readily according to the following reaction Schemes (in which all variables are as defined before) and Examples or modifications thereof using readily available starting materials, reagents and conventional synthesis procedures. In these reactions, it is also possible to make use of variants which are themselves known to those of ordinary skill in this art, but are not mentioned in greater detail.

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

Abbreviations used in the Examples are as follows:

| | |
|---|---|
| g = | grams |
| mg = | milligrams |
| L = | liters |
| mL = | milliliters |
| psi = | pounds per square inch |
| M = | molar |
| N = | normal |
| mM = | millimolar |
| i.v. = | intravenous |
| p.o. = | per oral |
| s.c. = | subcutaneous |
| Hz = | hertz |
| mol = | moles |
| mmol = | millimoles |
| mbar = | millibar |
| rt = | room temperature |
| min = | minutes |

-continued

| | |
|---|---|
| h = | hours |
| d = | days |
| mp = | melting point |
| TLC = | thin layer chromatography |
| R$_f$ = | relative TLC mobility |
| MS = | mass spectrometry |
| NMR = | nuclear magnetic resonance spectroscopy |
| APCI = | atmospheric pressure chemical ionization |
| ESI = | electrospray ionization |
| m/z = | mass to charge ratio |
| t$_r$ = | retention time |
| ether = | diethyl ether |
| MeOH = | methanol |
| EtOAc = | ethyl acetate |
| TEA = | triethylamine |
| DIEA = | diisopropylethylamine |
| BOP = | (1-benzotriazolyloxy)tris(dimethylamino)phosphonium hexafluorophosphate |
| THF = | tetrahydrofuran |
| DMF = | N,N-dimethylformamide |
| DMSO = | dimethylsulfoxide |
| LAH = | lithium aluminum hydride |
| TFA = | trifluoroacetic acid |
| EDC = | 1-ethyl-3-(3-dimethylaminopropyl)-carbodiimide hydrochloride |
| HOBt = | 1-hydroxybenzotriazole |
| LDA = | lithium diisopropylamide |
| THP = | tetrahydropyranyl |
| NMM = | N-methylmorpholine, 4-methylmorpholine |
| HMPA = | hexamethylphosphoric triamide |
| DMPU = | 1,3-dimethypropylene urea |
| DMAP = | 4-dimethylaminopyridine |
| DBU = | 1,8-diazabicyclo[5.4.0]undec-7-ene |
| ppm = | parts per million |
| kD = | kiloDalton |
| LPS = | lipopolysaccharide |
| PMA = | phorbol myristate acetate |
| SPA = | scintillation proximity assay |
| EDTA = | ethylenediamine tetraacetic acid |
| FBS = | fetal bovine serum |
| PBS = | phosphate buffered saline solution |
| ELISA = | enzyme-linked immunosorbent assay |

Several of the following examples represent pairs of stereoisomers which were separated as diastereoisomers but were not identified therein. Determination and/or preparation of the R and S isomers can advantageously be approached by stereoselective chemical methods, see "Advanced Organic Chemistry", Carey and Sundberg, 3rd edition, Plenum Press, 1990, 596, by analytical methods such as X-ray crystallography, or by determination of biological activity and subsequent correlation to biologically active compounds of known stereochemistry.

GENERAL REACTION SCHEMES

Compounds of the invention may be prepared by methods known in the art, where such a method is shown in reaction Scheme 1.

Reaction Scheme 1

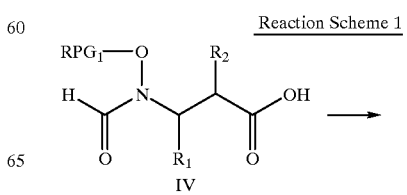

IV

31

-continued

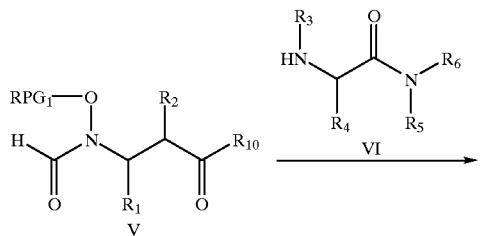

V

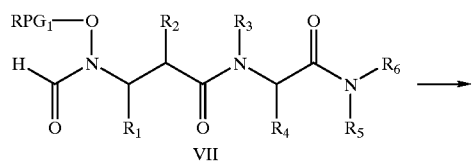

VII

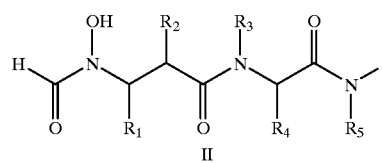

II $R_1$, $R_2$, $R_3$, $R_4$, $R_5$, and $R_6$ are defined as for formula (II).

$RPG_1$ is a protecting group suitable for the hydroxylamine oxygen, such as benzyl or 2-tetrahydropyranyl.

$R_{10}$ is chosen from the group consisting of hydroxyl, $O$—$C_6F_5$, or halogen.

When $R_{10}$ is hydroxyl, the conversion of (V) to (VII) involves methods known in peptide chemistry; for example, the reaction may be conducted using HOBt in combination with a dehydrating agent such as dicyclohexylcarbodiimide in a suitable solvent, such as DMF. When $R_{10}$ is O—$C_6F_5$, the conversion of (IV) to (V) is conducted by treating (IV) in a suitable solvent such as dichloromethane with pentafluorophenyl trifluoroacetate in the presence of pyridine, or with EDC and pentafluorophenol in a suitable solvent such as dichloromethane. The displacement reaction to produce (VII) is carried out in the presence of a suitable solvent such as dioxane, THF, dichloromethane, or DMF, at a temperature of 0° C. to 140° C. The reaction is effected in the presence of an organic base such as NMM or TEA. Further, the conversion of (IV) to (VII) may be carried out by reacting (IV) with a dialkyl cyanophosphonate in the presence of NMM or TEA in a solvent such as DMF, followed by addition of (VI). The removal of the $RPG_1$ group where $RPG_1$ is benzyl may be achieved by hydrogenation of (VII) with palladium on barium sulfate in a suitable solvent such as ethanol or THF, or, where $RPG_1$ is 2-tetrahydropyranyl, by hydrolysis with aqueous acetic acid at a temperature of 20° C. to 100° C.

Reaction Scheme 2 depicts the synthesis of a compound of formula (IV).

32

Reaction Scheme 2

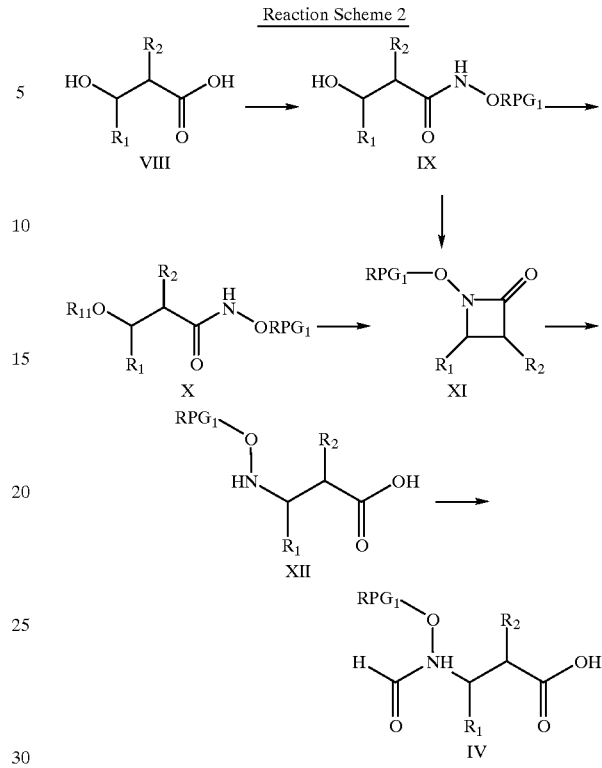

$R_1$ and $R_2$ are as defined for formula (II).

$R_{11}O$ is a nucleofugal group such as methanesulfonate or p-toluenesulfonate.

$RPG_1$ is as defined for reaction Scheme 1.

The acid of formula (VIII) may be converted to the alcohol of formula (IX) by treatment with HOBt, O-benzylhydroxylamine hydrochloride or O-(2-tetrahydropyranyl)hydroxylamine, NMM, and a carbodiimide reagent such as EDC in a suitable solvent such as DMF. The alcohol of formula (IX) may be converted to (X) by treatment with methanesulfonyl chloride or p-toluenesulfonyl chloride and pyridine in a suitable solvent such as dichloromethane. The conversion of (X) to (XI) may be conducted by treatment with potassium carbonate in a suitable solvent such as acetone or 2-butanone, at temperature of 20° C. to 90° C. Alternatively, (IX) may be converted directly to (XI) by treatment with triphenylphospbine and diethyl azodicarboxylate or another azodicarbonyl diester or diamide in a suitable solvent such as THF at a temperature of −78° C. to 50° C. The compound of formula (XI) may be converted to (XII) by treatment with an inorganic base such as sodium hydroxide in water or water in combination with a water—soluble organic cosolvent such as MeOH or THF, followed by acidification with an acidic solution such as aqueous citric acid or aqueous sodium bisulfate. The compound of formula (XII) may be converted to (IV) by treatment with acetic anhydride and formic acid or by treatment with formic acetic anhydride in pyridine in the presence or absence of a suitable cosolvent such as dichloromethane.

An alternate preparation of compounds of general formulae (XI) and (IV) is depicted in reaction Scheme 3.

Reaction Scheme 3

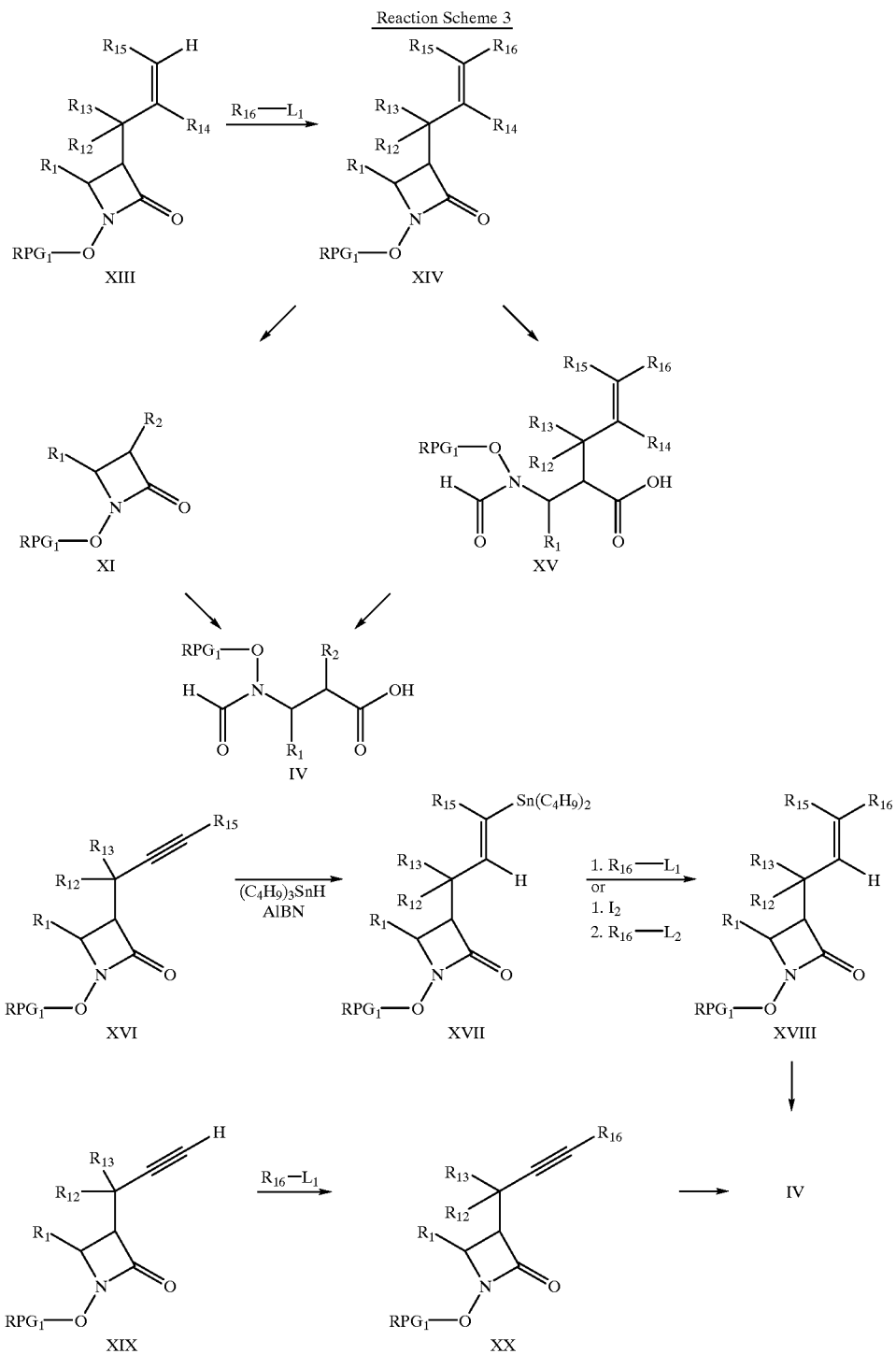

$R_1$ and $R_2$ are as defined as for formula (II).

$R_{12}$, $R_{13}$, $R_{14}$, and $R_{15}$ may be, independently, alkyl, alkenyl, alkynyl, or hydrogen.

$R_{16}$ is selected from the group consisting of aryl, heteroaryl, alkynyl, or alkenyl, with the proviso that the unsaturated carbons of alkenyl and alkynyl groups are directly bonded to $L_1$.

$L_1$ is selected from the group consisting of bromide, iodide, or trifluoromethanesulfonate.

$L_2$ is tri(lower alkyl)stannyl or $-B(OH)_2$.

$RPG_1$ is defined as for reaction scheme 1.

The lactam of general formula (XIII) may be treated with a palladium catalyst such as tetrakis(triphenylphosphine) palladium and $R_{16}-L_1$ in a solvent such as acetonitrile in the presence of a tertiary amine base such as NMM at a temperature of from 20° C. to 200° C. to afford (XIV). Reduction of the olefinic group in (XIV) with hydrogen and a metal catalyst such as palladium on carbon and conversion of the lactam (XI) to the acid (IV) proceeds as outlined in reaction Scheme 2. Alternately, the olefin in compounds of general formula (XIV) may be left in place and manipulation of the lactam (XIV) is carried out as described in reaction Scheme 2 to afford (XV). (XV) may be converted to (IV) as described in reaction Scheme 2 with or without reduction of the olefin in (XV), as appropriate. The alkyne (XVI) may be treated with tri(butyltin) hydride in the presence of a radical initiator such as azobis(isobutyronitrile) to afford an alkyl tin intermediate (XVII), which may be treated with $R_{16}$—$L_1$ and a catalyst such as $Pd(PPh_3)_4$ in a solvent such as DMF in the presence or LiCl to afford (XVIII). Alternately, (XVII) may be treated with iodine in an organic solvent such as ether to afford the destannylated vinyl iodide. The iodide may be treated with $R_{16}$—$L_2$ in the presence of a palladium catalyst such as $Pd(PPh_3)_4$ in a solvent such as DMF or THF at a temperature of 25° C. to 140° C. to afford (XVIII). The alkyne (XIX) may be treated with $R_{16}$—$L_1$, CuCl or CuI and alkylamine such as TEA in the presence of a catalyst such as $Pd(PPh_3)_4$ to afford (XX). (XX) and (XVIII) may be manipulated to the intermediate (IV) via the operations described previously.

An alternative route of preparation of compounds of formula (IX) is depicted in reaction Scheme 4.

Reaction Scheme 4

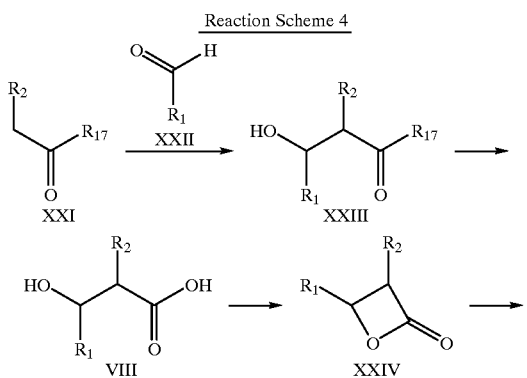

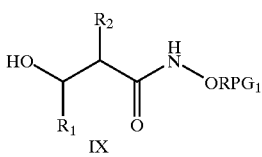

$R_1$ and $R_2$ are as defined as for formula (II).

$R_{17}$ is lower alkoxy or 1-oxazolidinyl.

$RPG_1$ is as defined for reaction Scheme 1.

A carbonyl compound of formula (XXI), where $R_{17}$ is an alkoxy group such as methoxy or tert-butoxy, may be treated with a strong base such as LDA in a solvent such as THF at a temperature of from −78° C. to 0° C., followed by treatment with the aldehyde (XXII) to provide (XXIII). Where $R_{17}$ is a oxazolidinon-1-yl substituent, treatment of (XXI) with a Lewis acid such as di(n-butyl)boron trifluoromethanesulfonate in the presence of DIEA in a suitable solvent such as dichloromethane at a temperature of 0° C., followed by addition of the aldehyde (XXII) provides (XXIII). Treatment of (XXIII) with aqueous base in the presence or absence of hydrogen peroxide affords (VIII) upon acidification. The acid (VIII) may be converted directly to (IX) as in reaction Scheme 2, or may be treated with a dehydrating agent such a p-toluenesulfonyl chloride in pyridine or with triphenylphosphine and diethyl azodicarboxylate in a suitable solvent such as THF, to afford the lactone (XXIV). Treatment of the lactone (XXIV) with $H_2NO$-$RPG_1$ in the presence of a Lewis acid such as trimethylaluminum in a suitable solvent such as toluene affords the alcohol (IX).

Reaction Scheme 5 depicts the preparation of compounds of general formula (VIII).

Reaction Scheme 5

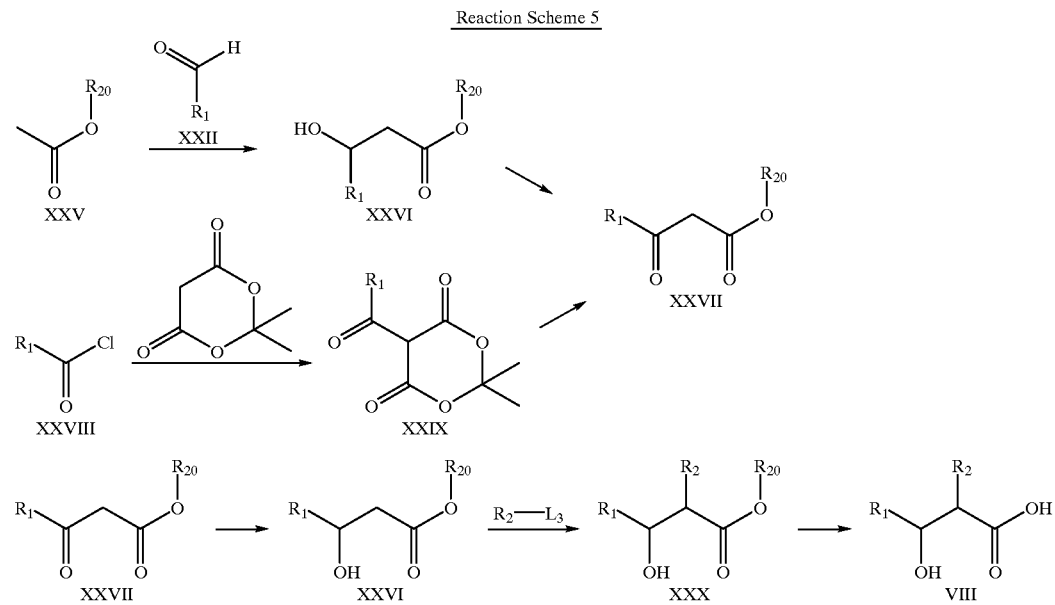

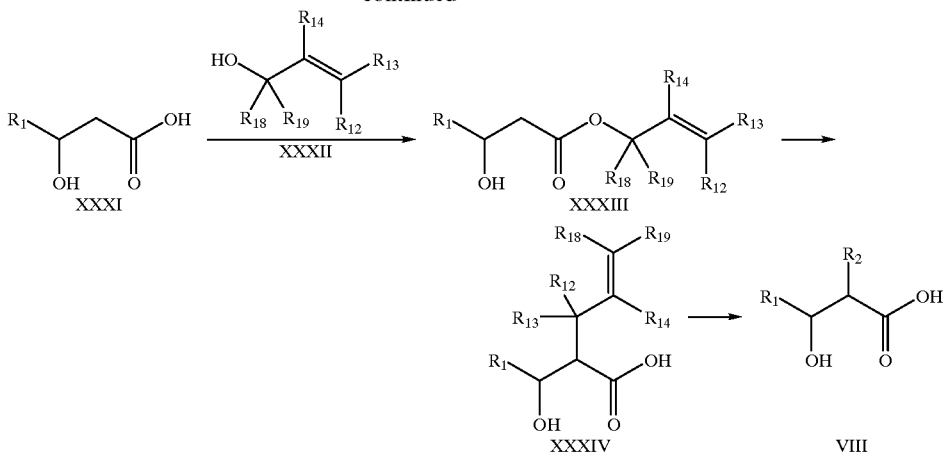

$R_1$ and $R_2$ are as defined for formula (II).
$R_{20}$ is lower alkyl.
$RPG_1$ is as defined for reaction Scheme 1.
$L_3$ is bromide, iodide, or trifluoromethanesulfonyloxy.
$R_{12}$, $R_{13}$ and $R_{14}$ are as defined for reaction scheme 3.
$R_{18}$ and $R_{19}$, may be, independently, alky, alkenyl, alkynyl, or hydrogen.

The ester of general formula (XXVI), if not commercially available, may be prepared by reaction of ester (XXV) with a strong base such as LDA followed by treatment with the aldehyde (XXII). The resulting hydroxyester (XXVI) may be used directly or converted to the ketoester (XXVII) by oxidation with, for example, pyridinium dichromate in a solvent such as dichloromethane. Alternately the acid chloride (XXVIII) may be condensed with 2,2-dimethyl-4,6-dioxo-1,3-dioxane in the presence of pyridine to afford (XXIX), which may be treated with excess $R_{20}$—OH at a temperature of from 25° C. to 150° C. to provide (XXVII). The ketoester of general formula (XXVII) may be reduced with a reducing agent such as sodium borohydride to afford the hydroxyester (XXVI). Alternately, a chiral catalyst or chiral ligand in the presence of a reducing agent such as hydrogen or a metal hydride such as borane or LAH may be employed to afford (XXVI) with chiral induction at the newly formed asymmetric center. The alcohol (XXVI) may be converted to (XXX) by treatment with a strong base such as LDA in a suitable solvent such as THF, followed by the addition of $R_2$—$L_3$ in the presence or absence of a cosolvent such as DMPU. Where $R_2$ contains an unsaturated group, (XXX) may be reduced with, for example, hydrogen and a noble metal catalyst, underappropriate conditions. Removal of the ester group by hydrolysis with aqueous hydroxide ion or, in the case where $R_{20}$ is tert-butyl, by treatment with a strong acid such as TFA, affords (VII). Hydroxy acid (XXXI) is obtained by hydrolysis of the ester group of (XXVI) with aqueous alkali. (XXXI) may be obtained by treatment of (XXVI) with TFA, where $R_{20}$ is tert-butyl. Coupling of the hydroxy acid (XXXI) with an allylic alcohol (XXXII) in the presence of a dehydrating agent such as EDC and a catalyst such as 4-dimethylaminopyridine provides the ester (XXXIII). Alternately, protection of the alcohol functionality of ester (XXVI) with, for example, a tert-butyldimethylsilyl group, may be required before processing of (XXVI) to the acid. Hydrolysis of the ester grouping of the protected (XXVI) as before followed by activation of the acid functionality as its acid chloride with oxalyl chloride and addition of the alcohol (XXXII) in the presence of an organic base such as TEA provides the ester (XXXIII) with the hydroxyl group protected. Deprotection of the hydroxyl group, if so protected, and treatment of the resulting ester (XXXIII) with a strong base such as LDA in a solvent such as 1,2-dimethoxyethane at a temperature of −78° C., followed by warming of the mixture to a temperature of between 0° C. and 90° C., followed by acidification of the mixture provides the acid (XXXIV). Reduction of the olefinic group in (XXXIV) with hydrogen and a metal catalyst such as palladium on carbon provides the acid (VIII). Alternately, the olefin in compounds of general formula (XXXIV) may be left in place until a later stage and then saturated with, for example, hydrogen gas in the presence of palladium on carbon.

The preparation of compounds of general formula (VI) is shown in reaction Scheme 6.

Reaction Scheme 6

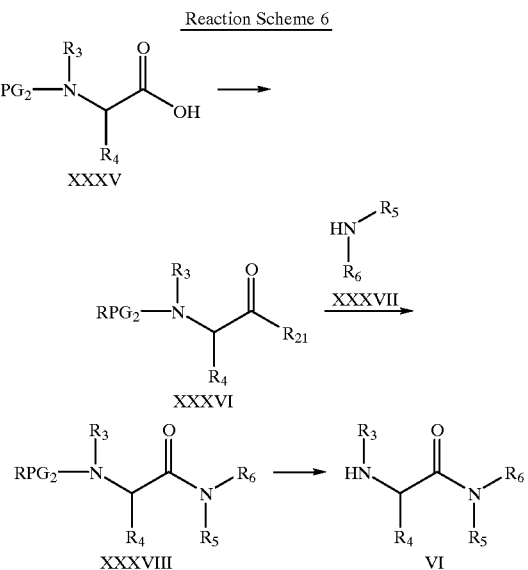

$R_3$, $R_4$, $R_5$, and $R_6$ are as defined for general formula (II).
$RPG_2$ is a protecting group such as tert-butoxycarbonyl or benzyloxycarbonyl.
$R_{21}$ is hydroxyl or halogen.

The acid of formula (XXXV) may be converted in situ to (XXXVI), where $R_{21}$ is bromide, by treatment with bromotris(pyrrolidino)phosphonium hexafluorophosphate in a suitable solvent such as DMF in the presence of an organic base such as DIEA. Addition of the amine (XXXVII) in the displacement step in the presence of a suitable solvent such as DMF and an organic base such as DIEA affords the amide (XXXVIII). Alternatively, the intermediate of formula (XXXVI) where $R_{21}$ is hydroxyl may be treated with carbonyldiimidazole in a solvent such as dichloromethane, followed by treatment with the amine (XXXVII) to afford (XXXVIII). Alternatively, the intermediate of formula (XXXV) may be treated with HOBt, the amine (XXXVII), an organic base such as NMM, and a carbodiimide reagent such as EDC in a suitable solvent such as DMF, at a temperature of 0° C. to 80° C. to provide (XXXVIII). The compound of formula (XXXVIII) may be converted to (VI) by deprotection, conditions being particular to the nature of $RPG_2$. For example, where $RPG_2$ is tert-butoxycarbonyl, conversion of (XXVIII) to (VI) may be accomplished by treatment of (XXVIII) with trifluoroacetic acid in the presence or absence of a suitable solvent such as dichloromethane, at a temperature of 0° C. to 50° C.

A preparation of compounds of general formula (XXXV) is shown in reaction Scheme 7.

$R_{22}$ is lower alkyl.

The compound (XXXIX) may be treated with an amidinating reagent such as 1-carboxamidino-3,5-dimethylpyrazole in a solvent such as DMF in the presence of tertiary base such as TEA to afford (XL). (XL) may be nitrated by treatment with nitric acid and sulfuric acid at a temperature of from 0° C. to 25° C. The nitrated product may be converted to (XXXV) by removal of $R_{22}$; for example, where $R_{22}$ is lower non tertiary alkyl, treatment with aqueous sodium hydroxide affords (XXXV). Concomitant removal of $R_{22}$ may occur spontaneously in the nitration step to provide (XXXV). The nitration procedure may afford (XLI) cleanly and (XLI) may be converted to (XXXV) by treatment with $RPG_2$—Cl and aqueous base (where $RPG_2$ is benzyloxycarbonyl), or $(RPG_2)_2O$ and aqueous base, where $RPG_2$ is tert-butoxycarbonyl. Alternately, the nitration procedure may afford (XLII) cleanly and (XLII) may be converted to (XXXV) by treatment with $RPG_2$—Cl and aqueous base (where $RPG_2$ is benzyloxycarbonyl), or $(RPG_2)_2O$ and aqueous base, where $RPG_2$ is tert-butoxycarbonyl; removal of the alkyl group $R_{22}$ by saponification with aqueous base (or, if appropriate and where $R_{22}$ is tert-butyl, by treatment with trifluoroacetic acid) provides (XXXV).

Reaction Scheme 7

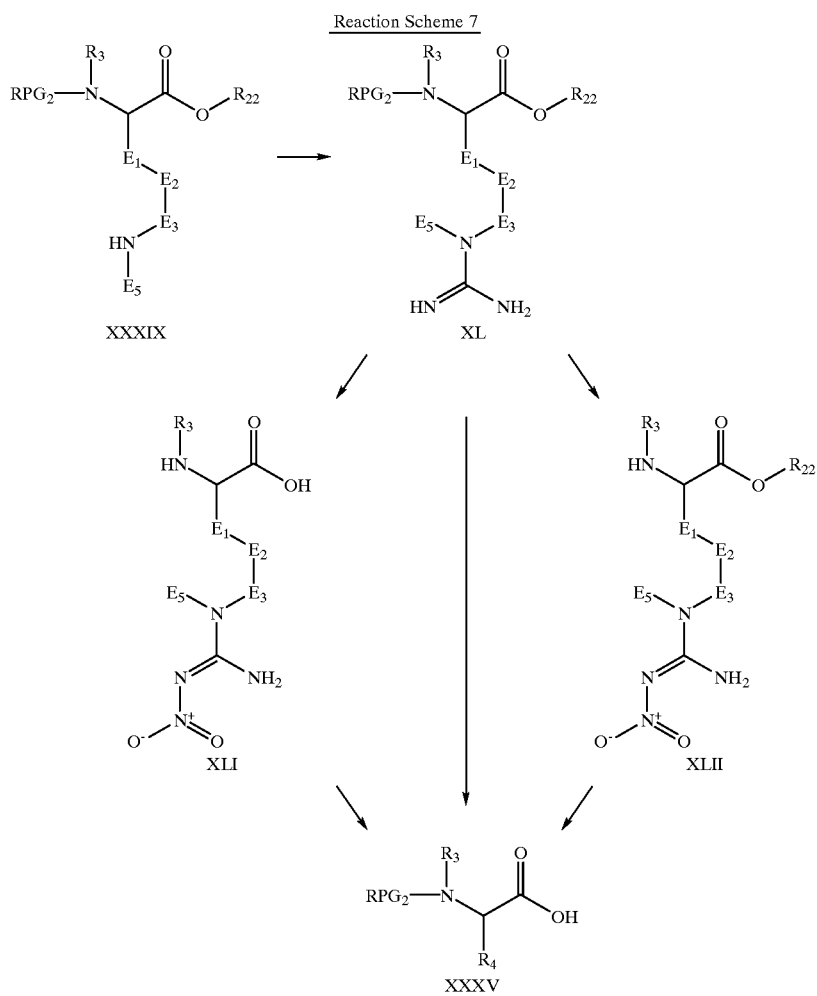

$R_3$, $R_4$, $E_1$, $E_2$, $E_3$, and $E_5$ are as defined for general formula (II).
$RPG_2$ is defined as for reaction scheme 6.

Reaction Scheme 8 depicts an alternate preparation of an intermediate of general formula (XXXV).

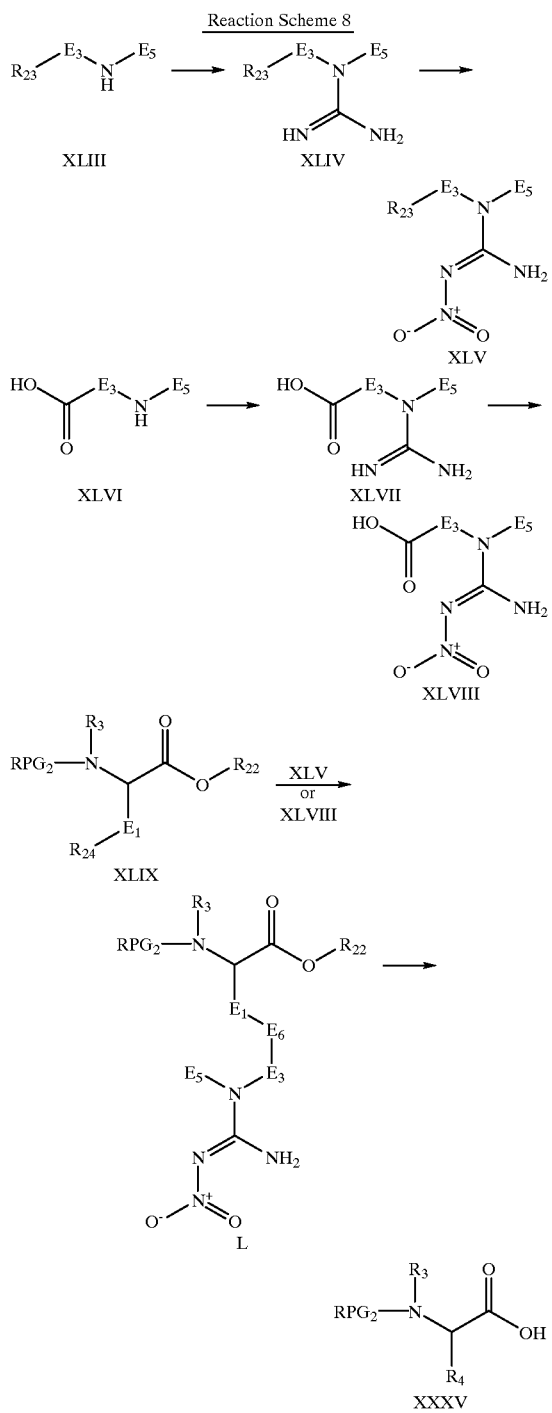

$R_3$, $R_4$, $E_1$, $E_3$, and $R_7$ are as defined for general formula (II).

$R_{24}$ is SH, $NR_7$, or OH.

$E_6$ is S, $NR_7$, OC(O), or O.

$RPG_2$ is defined as for reaction scheme 6.

$R_{22}$ is defined as for reaction scheme 7.

$R_{23}$ is bromide, iodide, methanesulfonate, or p-toluenesulfonate.

$R_{24}$ is hydrogen.

(XLIII) and (XLVI) may be treated with a amidinating reagent such as 1-carboxamidino-3,5-dimethylpyrazole in a solvent such as DMF in the presence of tertiary base such as TEA to afford (XLIV) and (XLVII), respectively. Nitration of (XLIV) and (XLVII) with nitric acid and sulfric acid at a temperature of between 0° C. and 25° C. affords (XLV) and (XLVIII), respectively. The ester (XLIX) may be treated with a) for the case where $R_{24}$ is OH, $NR_7$, or SH, (XLV) in the presence of a base such as sodium hydride or potassium carbonate in a suitable solvent such as DMF or THF, or b) for the case where $R_{24}$ is OH, or $NR_7$, (XLVII) in the presence of a dehydrating agent such as EDC in the presence of HOBt and NMM in a solvent such as DMP or $CHCl_2$, optionally in the presence of DMAP, to provide the intermediate of formula (L). Hydrolysis of the ester group as for reaction scheme 7 provides (XXXV).

Reaction scheme 9 depicts an alternate preparation of an intermediate of general formula (XXXIX).

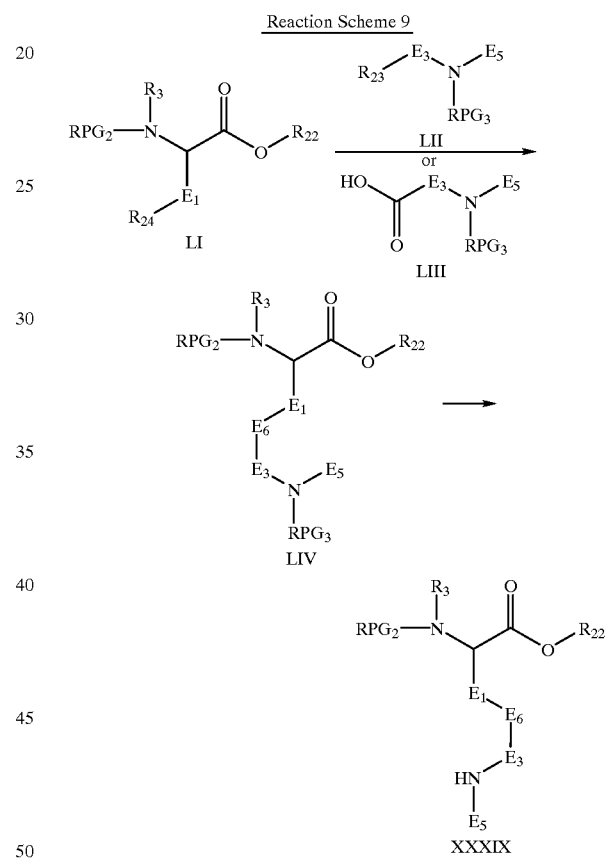

$R_3$, $E_1$, $E_2$, $E_3$, and $E_5$ are as defined for general formula (II).

$E_6$, $R_{23}$, and $R_{24}$ are defined as for reaction scheme 8.

$RPG_2$ is defined as for reaction scheme 6.

$R_{22}$ is defined as for reaction scheme 7.

$RPG_3$ is a protecting group such as tert-butoxycarbonyl or benzyloxycarbonyl.

The ester (LI) may be treated with a) for the case where $R_{24}$ is OH, $NR_7$, or SH, (LII) in the presence of a base such as sodium hydride or potassium carbonate in a suitable solvent such as DMF or THF, or b) for the case where $R_{24}$ is OH or $NR_7$, (LIII) in the presence of a dehydrating agent such as EDC in the presence of HOBt and NMM in a solvent such as DMF or dichloromethane, optionally in the presence of DMAP, to provide the intermediate of formula (LIV). Removal of $RPG_3$, by hydrogenation in the presence of palladium on carbon where $RPG_3$ is benzyloxycarbonyl, affords (XXXIX). Alternately, where $RPG_3$ is tert-butoxycarbonyl, $RPG_3$ may be removed by treatment with TFA to afford (XXXIX).

Reaction scheme 10 depicts an alternate preparation of an intermediate of general formula (XXXIX).

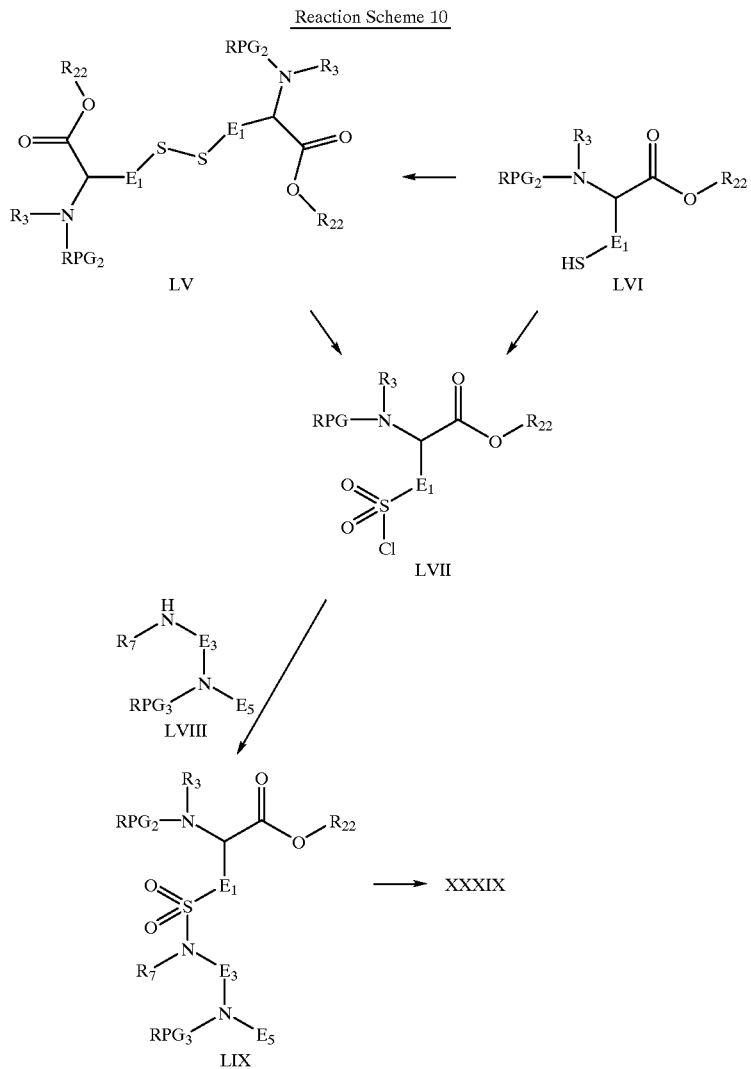

$R_3$, $R_4$, $R_7$, $E_1$, $E_3$, and $E_5$ are as defined for general formula (II).

$RPG_2$ is defined as for reaction scheme 6.

$R_{22}$ is defined as for reaction scheme 7.

$RPG_3$ is defined as for reaction scheme 9.

The thiol (LVI) may be oxidized to the disulfide (LV) by treatment with a mild base such as TEA and oxygen or air. Either the thiol (LVI) or the disulfide (LV) may be converted to the sulfonyl chloride (LVII) by treatment with chlorine gas in tetrachloromethane. Treatment of the sulfonyl chloride (LVII) with an amine (LVIII) in the presence of a tertiary amine base such as TEA or NMM affords (LIX). Removal of $RPG_3$, by hydrogenation in the presence of palladium on carbon where $RPG_3$ is benzyloxycarbonyl, affords (XXXIX). Alternately, where $RPG_3$ is tert-butoxycarbonyl, $RGP_3$ may be removed by treatment with TFA to afford (XXXIX).

Reaction scheme 11 depicts an alternate preparation of an intermediate of general formula (XXXIX).

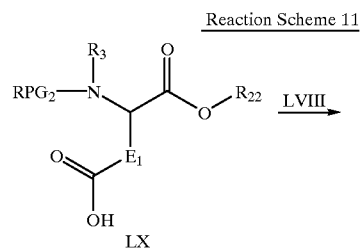

-continued

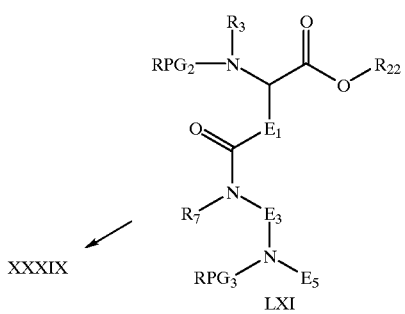

XXXIX $R_3$, $R_4$, $R_7$, $E_1$, $E_3$, and $E_5$ are as defined for general formula (II).

$RPG_2$ is defined as for reaction scheme 6.

$R_{22}$ is defined as for reaction scheme 7.

$RPG_3$ is defined as for reaction scheme 9.

Treatment of (LX) with the amine (LVIII) and a coupling reagent such as EDC or carbonyldiimidazole in the presence or absence of HOBt, in the presence of a tertiary amine base such as NMM in a solvent such as DMF affords (LXI). Removal of the $RPG_3$ protecting group as for reaction scheme 10 gives the amine (XXXIX).

Reaction Scheme 12 depicts an alternate preparation of an intermediate of general formula (XXXIX).

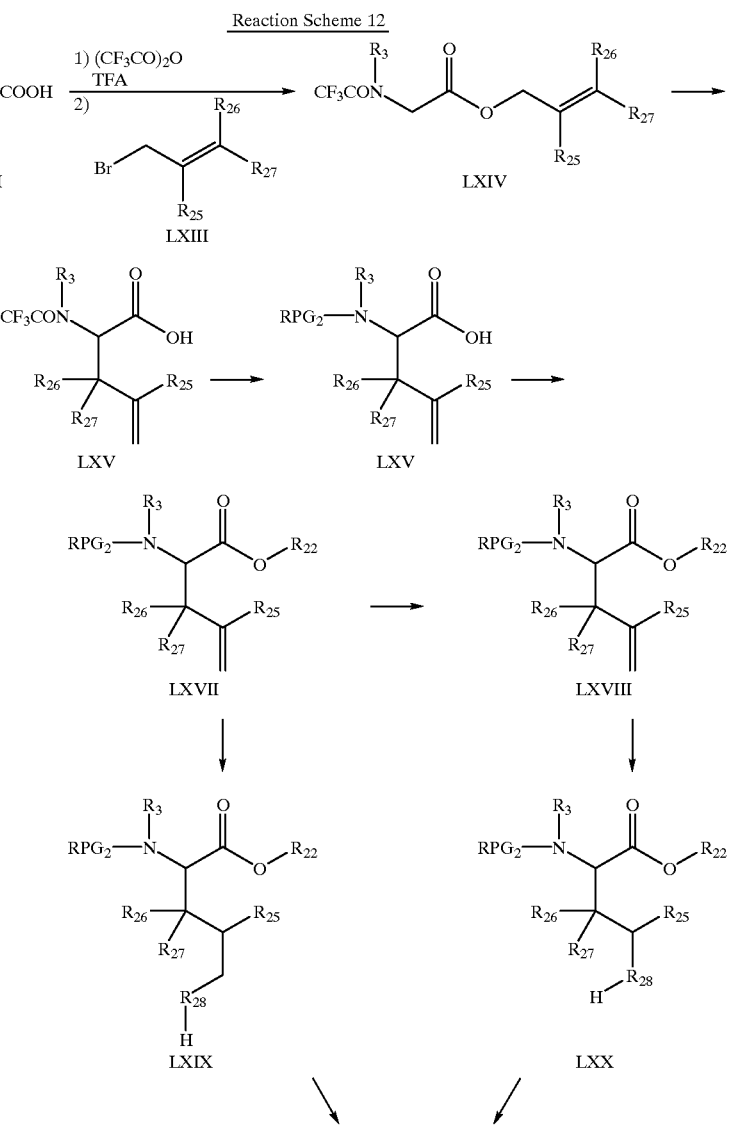

-continued

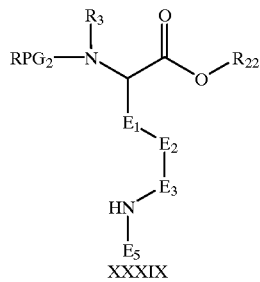

XXXIX $R_3$, $R_4$, $R_7$, $E_1$, $E_2$, $E_3$, and $E_5$ are as defined for general formula (II).

$RPG_2$ is defined as for reaction scheme 6.

$R_{22}$ is defined as for reaction scheme 7.

$R_{25}$ is alkcyl, alkenyl, alkynyl, cycloalkyl, or hydrogen.

$R_{26}$ and $R_{27}$ are, independently, alkyl, alkenyl, or alkynyl.

$R_{28}$ is O or NH.

$R_{25}$ and $R_{27}$ may be taken together to constitute a five to ten—membered ring.

$R_{26}$ and $R_{27}$ may be taken together to constitute a five to ten—membered ring.

The acid (LXII) is treated with trifluoroacetic anhydride and TFA to afford the trifluoroacetamide, which is then treated with the bromide (LXIII) and a base such as potassium carbonate in a solvent such as DMF to provide the ester (LXIV). (LXIV) is treated with LDA and aluminum triisopropoxide in the presence of quinidine or quinine in a solvent such as THF at a temperature of from −78° C. to 0° C. to afford (LXV) with a high degree of asymmetric induction. (LXV) is subjected to hydrolysis with aqueous base and the resulting amine is protected with $RPG_2$—Cl (where $RGP_2$ is benzyloxycarbonyl) or $(RPG_2)_2O$ (where $RPG_2$ is tert-butoxycarbonyl) and aqueous base. (LXVI) is then treated with $R_{22}$—Br and potassium carbonate in a solvent such as DMF to afford (LXVII). Alternately (LXVII) where $R_{22}$ is tert-butyl may be prepared by treatment with dimethylformamide di-tert-butyl acetal. (LXVII) may be treated with ozone in dichloromethane or dichloromethane/MeOH, followed by reduction with, for example, dimethyl sulfide to afford the carbonyl compound (LXVIII). (LXVIII) may be reduced with sodium borohydride to afford the alcohol (LXX) (where $R_{28}$ is O), which may be treated with methanesulfonyl chloride in pyridine to afford the methanesulfonate. The methanesulfonate may be then treated with sodium azide in a solvent such as DMF at a temperature of from 25° C. to 120° C. to afford the azide, which may be reduced with, for example, palladium and hydrogen gas to provide (LXX) where $R_{28}$ is NH. The olefin in (LXVII) may be hydroborated with, for example, tert-hexylborane and the intermediate oxidized with alkaline hydrogen peroxide to afford (LXIX) where $R_{28}$ is O. $R_{28}$ may be converted to NH as described above. $R_{28}$ may be further manipulated to afford the intermediate of general structure (XXXIX). Selection of $R_{22}$ as tert-butyl and $RPG_2$ as benzyloxycarbonyl is optimal for the preparation of (XXXIX) according to reaction scheme 12.

Reaction scheme 13 depicts an alternate preparation of an intermediate of general formula (VI).

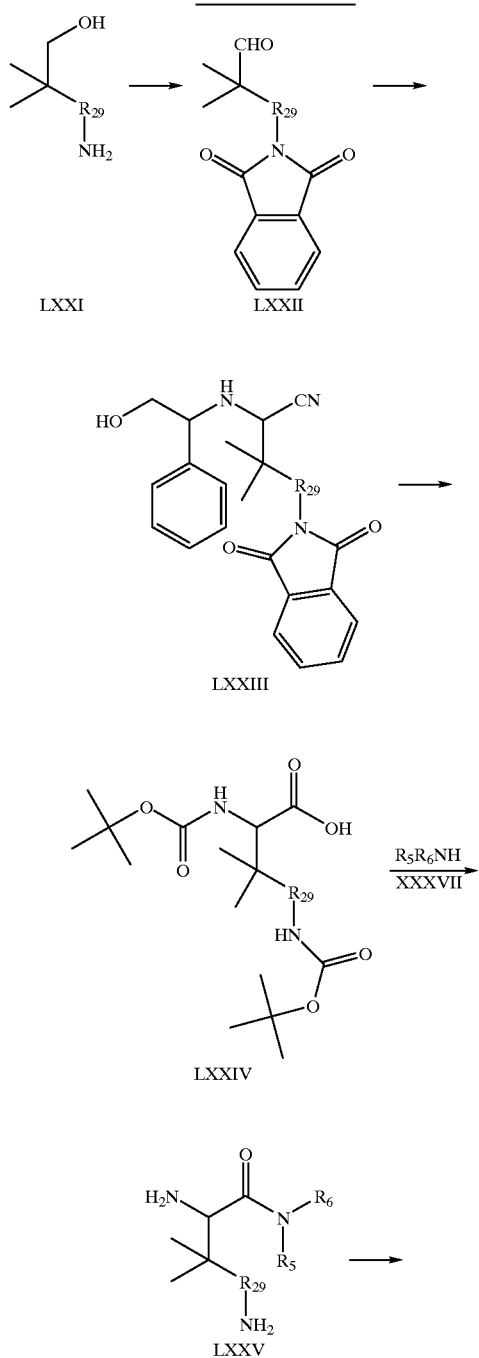

Reaction Scheme 13

-continued

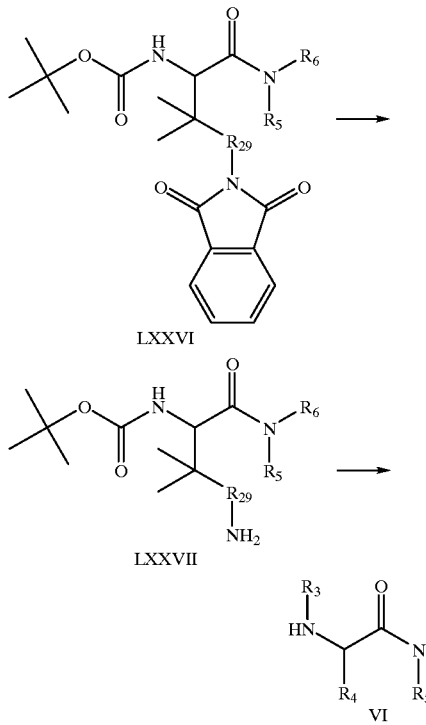

LXXVI

LXXVII

VI $R_3$, $R_4$, $R_5$, and $R_6$ are as defined for general formula (II). $R_{29}$ is alkylene, alkenylene, alkynylene, cycloalkylene, cycloalkenylene, heterocyclylene, arylene, or heteroarylene.

The amino alcohol (LXXI) is treated with phthalic anhydride in a solvent such as toluene at a temperature of from 25° C. to 120° C., or with N-ethoxycarbonylphthalimide and sodium bicarbonate at a temperature of from −20° C. to 45° C., followed by oxidation of the resulting phthalimido alcohol with an oxidizing agent such as pyridinium chlorochromate to provide the aldehyde (LXXII). Treatment of (LXXII) with trimethylsilyl cyanide and phenylglycinol affords (LXXIII). Use of enantiopure phenylglycinol in this operation may induce chirality in (LXXIIII), which may be preserved in the subsequent steps of reaction scheme 13. Treatment of (LXXIII) with 12 N HCl at a temperature of 25° C. to 70° C. is followed by treatment with hydrazine and acidification with 1 N HCl. The product is treated in a solvent such as MeOH with palladium hydroxide on carbon under 60 psi of hydrogen pressure at a temperature of from 25° C. to 80° C., followed by treatment with di-tert-butyl dicarbonate and aqueous sodium hydroxide to afford (LXXIV) after acidification. Treatment of (LXXIV) with the amine (XXXVII) and a dehydrating agent such as EDC in the presence of HOBt in a solvent such as DMF at a temperature of 0° C. to 25° C., followed by treatment with HCl in a solvent such as dichloromethane or dioxane affords (LXXV). Treatment of (LXXV) with N-ethoxycarbonylphthalimide in a solvent such as DMF with TEA at a temperature of −20° C., followed by treatment of the product with di-tert-butyl dicarbonate and DMAP in a solvent such as dichloromethane affords (LXXVI). (LXXVI) may be treated with hydrazine in a solvent such as MeOH or ethanol to provide (LXXVII). (LXXVII) may be manipulated (amidination, nitration) as described in previous reaction schemes to afford an intermediate of formula (VI).

PHARMACEUTICAL FORMULATION AND DOSES

The compounds of the present invention can be administered in such oral (including buccal and sublingual) dosage forms as tablets, capsules (each including timed release and sustained release formulations), pills, powders, granules, elixirs, tinctures, suspensions, syrups and emulsions. Likewise, they may also be administered in nasal, ophthalmic, otic, rectal, topical, intravenous (both bolus and infusion), intraperitoneal, intraarticular, subcutaneous or intramuscular inhalation or insufflation form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.1 to 2000 mg/kg of body weight per day, and particularly 1 to 100 mg/kg of body weight per day. Oral dosage units will generally be administered in the range of from 1 to about 250 mg and more preferably from about 25 to 250 mg. The daily dosage for a 70 kg mammal will generally be in the range of about 10 mg to 5 grams of a compound of formula I or II.

While the dosage to be administered is based on the usual conditions such as the physical condition of the patient, age, body weight, past medical history, route of administrations, severity of the conditions and the like, it is generally preferred for oral administration to administer to a human. In some cases, a lower dose is sufficient and, in some cases, a higher dose or more doses may be necessary. Topical application similarly may be once or more than once per day depending upon the usual medical considerations. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.1 to 99.5%, more particularly, 0.5 to 90% of a compound of the formula (II) in combination with a pharmaceutically acceptable carrier.

Parenteral administration can be effected by utilizing liquid dosage unit forms such as sterile solutions and suspensions intended for subcutaneous, intramuscular, intrathecal, intrarterial or intravenous injection. These are prepared by suspending or dissolving a measured amount of the compound in a non-toxic liquid vehicle suitable for injection such as aqueous oleaginous medium and sterilizing the suspension or solution.

Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservations and emulsifiers can also be added.

Rectal administration can be effected utilizing suppositories in which the compound is admixed with low-melting water-soluble or insoluble solids such as polyethylene glycol, cocoa butter, higher ester as for example flavored aqueous solution, while elixirs are prepared through myristyl palmitate or mixtures thereof.

Topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The preferred pharmaceutical compositions are those in a form suitable for oral administration, such as tablets and liquids and the like and topical formulations.

EXAMPLES

The following examples are illustrative embodiments of the invention, not limiting the scope of the invention in any way. Reagents are commercially available or are prepared according to procedures in the literature.

Example 1

(2R,3S)-3-(Formyl-hydroxyamino)-2-(2-methyl-1-propyl)hexanoic Acid [(1S)-4-(nitroimino-amino)methylamino-1-(1,3-thiazol-2-ylcarbamoyl)-1-butyl]amide

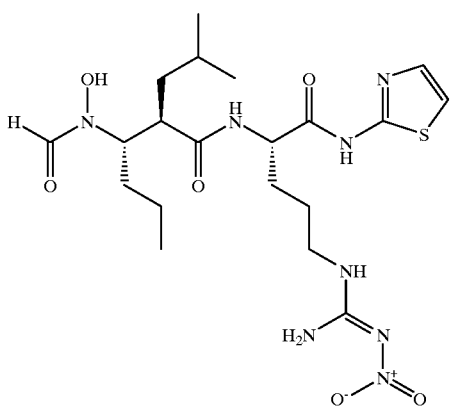

Example 1a

Ethyl (3R)-3-Hydroxyhexanoate and Methyl (3R)-3-Hydroxyhexanoate

Ethyl butyrylacetate (50.0 g, 316 mmol) is stirred in 75 mL of absolute ethanol as [RuCl$_2$(BINAP)]$_2$•NEt$_3$ (0.139 g, 0.158 mmol) is added along with 2 N hydrochloric acid (0.158 mL, 0.316 mmol). The mixture is placed on a pressure hydrogenation apparatus and degassed by evacuating and filling with nitrogen several times. The vessel is then pressurized with hydrogen to 65 psi. The reaction is heated to 70° C. for 36 h and then is allowed to cool to 25° C. The resulting reddish brown solution is concentrated under reduced pressure and the product distilled (40–50° C., 200 millitorr) to give a clear oil (50.0 g, 99% yield, >99% enantiomeric excess determined by chiral analytical HPLC).

$^1$H NMR (400 MHz, CDCl$_3$) δ 4.17 (q, 2H), 4.01 (m, 1H), 2.95 (d, 1H), 2.47 (dd, 1H), 2.40 (dd, 1H), 1.58–1.38 (m, 4H), 1.38 (t, 3H), 0.94 (t, 3H) ppm.

Methyl (3R)-3-hydroxyhexanoate is prepared in the same manner described above in methanol employing methyl butyrylacetate as the starting ketoester. The enantiomeric excess is 99% as determined by chiral analytical HPLC methods.

$^1$H NMR (300 MHz, CDCl$_3$) δ 4.04 (m, 1H), 3.72 (s, 3H), 2.87 (d, 1H), 2.50 (dd, 1H), 2.46 (dd, 1H), 1.58–1.38 (m, 4H), 0.94 (t, 3H) ppm.

Example 1b

Methyl (2R,3R)-2-(2-Methyl-2-propene-1-yl)-3-hydroxyhexanoate

To a stirred solution of diisopropylamine (19.4 mL, 139 mmol) in 70 mL of THF at −78° C. is added dropwise 86.6 mL (139 mmol) of 1.6 M n-butyllithium in hexanes over 15 min. After 1 h, a solution of methyl (3R)-3-hydroxyhexanoate (9.2 g, 63 mmol) in 10 mL of THF is added dropwise over several minutes. The reaction mixture is stirred 1 h, then treated with a solution of 3-bromo-2-methyl-1-propene (7.6 mL, 75.6 mmol) in 10 mL of HMPA and is allowed to stand at −20° C. overnight. The reaction mixture is poured into ice-cold 1 N hydrochloric acid (300 mL) and extracted with two 200-mL portions of EtOAc. The combined organic layers are washed with two 100-mL portions of saturated aqueous sodium chloride, dried over sodium sulfate, and filtered. The solvents are removed under reduced pressure. Purification by flash chromatography on silica gel eluting with 10% EtOAc-hexanes affords 7 g (55%) of methyl (2R,3R)-2-(2-methyl-2-propene-1-yl)-3-hydroxyhexanoate as an oil.

TLC R$_f$ (hexanes-EtOAc, 1:1) 0.75. $^1$H NMR (300 MHz, CDCl$_3$) δ 4.82 (s, 1H), 4.75 (s, 1H), 3.70 (s, 3H), 3.68 (m, 1H), 2.70 (m, 1H), 2.50 (m, 1H), 2.35 (dd, 1H), 1.75 (s, 3H), 1.60–1.65 (m, 4H), 0.95 (t, 3H) ppm.

Example 1c

Methyl (2R,3R)-2-(2-Methyl-1-propyl)-3-hydroxyhexanoate

A mixture of methyl (2R,3R)-2-(2-methyl-2-propene-1-yl)-3-hydroxyhexanoate (7 g, 34.6 mmol) and 1.7 g of 5% palladium on carbon (50 wt. % water content) in 50 mL of MeOH is stirred overnight under hydrogen gas at 1 atmosphere pressure. Filtration and concentration of the filtrate under reduced pressure affords 6.5 g (93%) of methyl (2R,3R)-2-(2-methyl-1-propyl)-3-hydroxyhexanoate as an oil.

TLC R$_f$ (hexanes-EtOAc, 1:1) 0.75. $^1$H NMR (300 MHz, CDCl$_3$) δ 3.75 (s, 3H), 3.65 (m, 1H), 2.57 (m, 1H), 2.10 (bs, 1H), 1.80–1.23 (m, 7H), 0.90 (m, 9H) ppm.

Example 1d (2R,3R)-2-(2-Methyl-1-propyl)-3-hydroxyhexanoic Acid

A solution of methyl (2R,3R)-2-(2-methyl-1-propyl)-3-hydroxyhexanoate (6.5 g, 31.9 mmol) in 100 mL of water—MeOH—THF (1:1:4) is treated with lithium hydroxide monohydrate (1.6 g, 38 mmol) and stirred overnight. The reaction mixture is acidified to pH 2 using 1 M aqueous sodium hydrogen sulfate and extracted with two 100-mL portions of EtOAc. The combined organic layers are washed with two 25-mL portions of saturated aqueous sodium chloride, dried over sodium sulfate and filtered, and the solvents are removed under reduced pressure. Purification by flash chromatography on silica gel eluting with 10% EtOAc-hexanes affords 6.0 g (100%) of (2R,3R)-2-(2-methyl-1-propyl)-3-hydroxyhexanoic acid as a gum.

$^1$H NMR (300 MHz, CDCl$_3$) δ 3.65 (m, 1H), 2.57 (m, 1H), 1.80–1.30 (m, 7H), 0.95 (m, 9H) ppm.

Example 1e (2R,3R)-2-(2-Methyl-1-propyl)-3-hydroxyhexanoic Acid 2-Tetrahydropyranyloxyamide To a stirred solution of (2R,3R)-2-(2-methyl-1-propyl)-3-hydroxyhexanoic acid (6.0 g, 32.3 mmol) in 33 mL of dichloromethane at 0° C. is added 2-tetrahydropyranyloxyamine (7.70 g, 65.8 mmol) followed by EDC (7.50 g, 39.4 mmol). The reaction mixture is allowed to warm to 25° C., stirred 12 h, then diluted with 100 mL of EtOAc and washed successively with 50 mL each of water, 1 M aqueous sodium bisulfate solution, saturated aqueous sodium bicarbonate and saturated aqueous sodium chloride. The combined organic layers are dried over sodium sulfate and filtered, and the solvents are removed under reduced pressure. Purification by flash chromatography on silica gel eluting with 10% EtOAc-hexanes affords 9.0 g (97%) of (2R,3R)-2-(2-methyl-1-propyl)-3-hydroxyhexanoic acid 2-tetrahydropyranyloxyamide as a gum.

TLC $R_f$ (hexanes-EtOAc, 1:1) 0.60. $^1$H NMR (300 MHz, CDCl$_3$) δ 8.90 (d, 1H), 5.00 (2 s, 1H), 4.00 (m, 1H), 3.62 (m, 2H), 3.01 (t, 1H), 2.21 (m, 1H), 1.90–1.30 (m, 13H), 0.92 (m, 9H) ppm.

Example 1f (3R,4S)-3-(2-Methyl-1-propyl)-4-propyl-1-(2-tetrahydropyranyloxy)azetidin-2-one To a stirred solution of (2R,3R)-2-(2-methyl-1-propyl)-3-hydroxyhexanoic acid 2-tetrahydropyranyloxyamide (9.0 g, 31.3 mmol) in 50 mL of anhydrous pyridine at 0° C. is added methanesulfonyl chloride (2.9 mL, 37.6 mmol). The reaction mixture is allowed to stand at 5° C. overnight and the pyridine is removed under reduced pressure. The resulting gum is dissolved in EtOAc (200 mL) and washed successively with 50 mL each of ice-cold 0.1 N hydrochloric acid, dilute aqueous sodium carbonate, and saturated aqueous sodium chloride. The combined organic extracts are dried over sodium sulfate and filtered, and the solvents are removed under reduced pressure affording the methanesulfonate as an off-white solid (11.6 g, 98%) which is used without further purification.

TLC $R_f$ (hexanes-EtOAc, 1:1) 0.75. $^1$H NMR (300 MHz, CDCl$_3$) δ 5.00 (m, 1H), 4.81 (m, 1H), 4.00 (m, 1H), 3.60 (bt, 1H), 3.05 (s, 3H), 2.76–2.60 (m, 1H), 1.92–1.11 (m, 13H), 0.91 (m, 9H) ppm.

A mixture of powdered potassium carbonate (15.0 g, 109 mmol) in 200 mL of acetone is refluxed for 0.5 h then treated with a solution of the above methanesulfonate in 100 mL of acetone and refluxed for an additional 48 h. The resulting slurry is filtered to remove salts and the filtrate is concentrated under reduced pressure. The crude oil is dissolved in 200 mL of EtOAc and washed successively with 50 mL of water and 50 mL of saturated aqueous sodium chloride and the combined organic extracts are dried over sodium sulfate. Filtration and removal of the solvents under pressure affords 8.2 g (96%) of (3R,4S)-3-(2-methyl-1-propyl)-4-propyl-1-(2-tetrahydropyranyloxy)azetidin-2-one as a 1:1 mixture of diastereomers which is used without further purification.

TLC $R_f$ (hexanes-EtOAc, 9:1) 0.30. $^1$H NMR (300 MHz, CDCl$_3$) δ 5.20 and 5.04 (two m, 1H), 4.27 and 4.50 (two dt, 1H), 4.01–3.89 (m, 1H), 3.68 (m, 1H), 3.05 (m, 1H), 1.92–1.30 (m, 13H), 1.00 (m, 9H) ppm.

Example 1g (2R,3S)-3-(2-Tetrahydropyranyloxyamino)-2-(2-methyl-1-propyl)hexanoic Acid A solution of the lactam (3R,4S)-3-(2-methyl-1-propyl)-4-propyl-1-(2-tetrahydropyranyloxy)azetidin-2-one (8.2 g, 30.5 mmol) in 90 mL of dioxane is treated with 53 mL of aqueous 3 N aqueous sodium hydroxide and stirred at 25° C. for 24 h. The reaction mixture is adjusted to pH 2 with 1 M aqueous sodium bisulfate and then extracted with two 100-mL portions of EtOAc. The combined organic extracts are dried over sodium sulfate and filtered, and the solvents are removed under reduced pressure affording 7.9 g (90%) of crude (2R,3S)-3-(2-tetrahydropyranyloxyamino)-2-(2-methyl-1-propyl)hexanoic acid as a viscous oil which is used without further purification.

$^1$H NMR (300 MHz, CDCl$_3$) δ 8.80 (bs, 1H), 4.85 and 4.75 (two m, 1H), 3.95 (m, 1H), 3.60 (m, 1H), 3.19 and 2.87 (two m, 1H), 3.05 (m, 1H), 1.95–1.12 (m, 13H), 0.91 (m, 9H) ppm.

Example 1h (2R,3S)-3-(Formyl-2-tetrahydropyranyloxyamino)-2-(2-methyl-1-propyl)hexanoic Acid A solution of (2R,3S)-3-(2-tetrahydropyranyloxyamino)-2-(2-methyl-1-propyl)hexanoic acid (7.90 g, 27.5 mmol) in 100 mL of anhydrous pyridine is cooled to 0° C. and treated with formic acetic anhydride (4.0 mL, 46 mmol). The reaction mixture is allowed to warm to 25° C., stirred for 6 h, and then concentrated to dryness under reduced pressure. The resulting gum is dissolved in 150 mL of EtOAc and washed successively with two 50-mL portions of 1 M aqueous sodium bisulfate and two 50-mL portions of saturated aqueous sodium chloride. The combined organic extracts are dried over sodium sulfate and filtered, and the solvents are removed under reduced pressure affording 8.67 g (99%) of (2R,3S)-3-(formyl-2-tetrahydropyranyloxyamino)-2-(2-methyl-1-propyl)hexanoic acid obtained as a viscous oil.

$^1$H NMR (300 MHz, CDCl$_3$) δ 8.68 and 8.56 (d and s, 1H), 5.07 and 4.81 (two s, 1H), 4.40 (m, 1H), 4.00 (m, 1H), 3.62 (m, 1H), 2.90 and 2.72 (two t, 1H), 2.00–1.20 (m, 13H), 0.98 (m, 9H) ppm.

Example 1i (2S)-2-tert-Butoxycarbonylamino-5-(nitroimino-amino)methylaminopentanoic Acid 1,3-Thiazol-2-ylamide To a stirred solution of (2S)-2-tert-butoxycarbonylamino-5-(nitroimino-amino)methylaminopentanoic acid (5.00 g, 15.6 mmol) and 2-aminothiazole (1.72 g, 17.2 mmol) in DMF (16 mL) is added EDC (3.30 g, 17.2 mmol). The solution is allowed to stir for 4 h then added to half-saturated aqueous sodium chloride solution and extracted with EtOAc. The combined organic extracts are washed with 1 N sodium bisulfate, 5% aqueous sodium bicarbonate, saturated aqueous sodium chloride, and dried over magnesium sulfate. Concentration in vacuo provides (2S)-2-tert-butoxycarbonylamino-5-(nitroimino-amino)methylaminopentanoic acid 1,3-thiazol-2-ylamide as a solid (2.28 g, 36%).

$^1$H NMR (CD$_3$OD, 400 MHz) δ 7.42 (d, 1H), 7.10 (d, 1H), 4.31 (m, 1H), 3.29 (m, 2H), 1.85 (m, 1H), 1.71 (m, 2H), 1.41 (s, 9H), 1.33 (m, 1H) ppm.

Example 1j (2S)-2-Amino-5-(nitroimino-amino)methylaminopentanoic Acid 1,3-Thiazol-2-ylamide Hydrochloride (2S)-2-tert-Butoxycarbonylamino-5-(nitroimino-amino)methylaminopentanoic acid 1,3-thiazol-2-ylamide (2.28 g,

57

5.68 mmol) is dissolved in 5 mL THF and 5 mL 4 N HCl in dioxane. After 3 h, dichloromethane is added and the mixture is filtered. The semisolid is collected and is treated with methanol—toluene and concentrated in vacuo; this process is repeated several times to afford 1.63 g of (2S)-2-amino-5-(nitroimino-amino)methylaminopentanoic acid 1,3-thiazol-2-ylamide hydrochloride as a solid.

$^1$H NMR (DMSO-$d_6$, 300 MHz) δ 8.58 (bs, 4H), 7.99 (bs, 1H), 7.52 (d, 1H), 7.31 (d, 1H), 6.4–5.9 (bs, 2H), 4.08 (m, 1H), 3.17 (bs, 2H), 1.83 (m, 2H), 1.53 (m, 2H) ppm. ESI-MS m/z 302 (M+H)$^+$.

Example 1k (2R,3S)-3-(Formyl-2-tetrahydropyranyloxyamino)-2-(2-methyl-1-propyl)hexanoic Acid [(1S)-4-(nitroimino-amino)methylamino-1-(1,3-thiazol-2-ylcarbamoyl)-1-butyl]amide To a 0° C. solution of (2R,3S)-3-(formyl-2-tetrahydropyranyloxyamino)-2-(2-methyl-1-propyl)hexanoic acid (172 mg, 0.546 mmol) in 1 mL DMF is added diethyl cyanophosphonate (98 mg, 0.60 mmol) followed by NMM (61 mg, 0.60 mmol). Stirring is continued for 30 min at 0° C. (2S)-2-Amino-5-(nitroimino-amino)methylaminopentanoic acid 1,3-thiazol-2-ylamide hydrochloride (203 mg, 0.60 mmol) is added followed by additional NMM (122 mg, 1.20 mmol). The mixture is heated at 40° C. for 16 h then allowed to cool to 25° C. The reaction mixture is added to half-saturated aqueous sodium chloride and extracted with 1:1 EtOAc-diethyl ether. The combined organic layers are washed with pH 4.3 phosphate buffer, 5% aqueous sodium bicarbonate, saturated aqueous sodium chloride, and dried over magnesium sulfate. Concentration and chromatography on silica gel (5% methanol-dichloromethane) provides 166 mg of (2R,3S)-3-(formyl-2-tetrahydropyranyloxyamino)-2-(2-methyl-1-propyl)hexanoic Acid [(1S)-4-(nitroimino-amino)methylamino-1-(1,3-thiazol-2-ylcarbamoyl)-1-butyl]amide as a foam.

ESI-MS m/z 599 (M+H)$^+$, 621 (M+Na)$^+$.

Example 1

(2R,3S)-3-(Formyl-hydroxyamino)-2-(2-methyl-1-propyl)hexanoic Acid [(1S)-4-(nitroimino-amino)methylamino-1-(1,3-thiazol-2-ylcarbamoyl)-1-butyl]amide (2R,3S)-3-(Formyl-2-tetrahydropyranyloxyamino)-2-(2-methyl-1-propyl)hexanoic acid [(1S)-4-(nitroimino-amino)methylamino-1-(1,3-thiazol-2-ylcarbamoyl)-1-butyl]amide (166 mg) is dissolved in 2 mL 80% acetic acid and heated at 40° C. for 20 h. Concentration in vacuo and trituration in dichloromethane—ether provides (2R,3S)-3-(formyl-hydroxyamino)-2-(2-methyl-1-propyl)hexanoic acid [(1S)-4-(nitroimino-amino)methylamino-1-(1,3-thiazol-2-ylcarbamoyl)-1-butyl]amide as a solid (106 mg, 74%).

Mp 130–136° C. Anal. Calcd. for $C_{20}H_{34}N_8O_6S$: C, 46.68; H, 6.66; N, 21.78; S, 6.23; Found: C, 46.45; H, 6.75; N, 21.60; S, 6.14.

58

Example 2

(2R,3S)-3-(Formyl-hydroxyamino)-2-(cyclohexylmethyl)hexanoic Acid [(1S)-4-(nitroimino-amino)methylamino-1-(1,3-thiazol-2-ylcarbamoyl)-1-butyl]amide

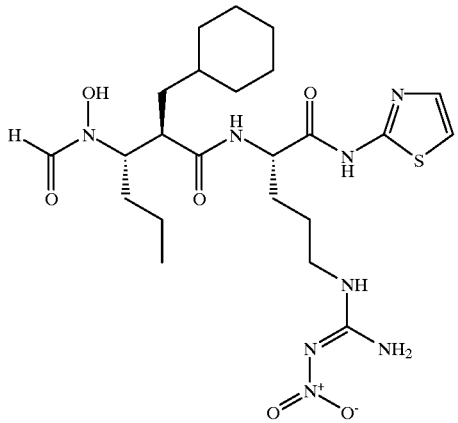

Example 2a

Ethyl (2R,3R)-2-Cyclohexylmethyl-3-hydroxyhexanoate

Diisopropylamine (5.89 mL, 44.9 mmol) is dissolved in 30 mL of anhydrous 1T and chilled to 0° C. n-Butyllithium (16.5 mL of a 2.5 M solution in hexanes, 41.2 mmol) is added dropwise over 10 min and the resulting pale yellow solution cooled to −78° C. A 15-mL THF solution of ethyl (3R)-3-hydroxyhexanoate (3.00 g, 18.7 mmol) is added over 10 min and stirred for 30 min. Cyclohexylmethyl iodide (6.29 g, 28.05 mmol) is dissolved in 20 mL of a 1:1 THF/HMPA solution and added to the dianion at −78° C. dropwise. The resulting solution is allowed to warm slowly to 0° C. over 3 h After stirring overnight at 4° C. 250 mL of a 5% aqueous citric acid solution is added and the mixture is extracted with two 250-mL portions of ether. The combined organics are washed -with saturated aqueous sodium chloride, dried over sodium sulfate, and concentrated in vacuo. The crude product is chromatographed on silica gel (elution with 25% EtOAc-hexanes) to provide ethyl (2R,3R)-2-cyclohexylmethyl-3-hydroxybexanoate (1.44 g, 30% yield) as an oil.

$^1$H NMR (300 MHz, CDCl$_3$) δ 4.15 (q, 2H), 3.65 (m, 1H), 2.60 (m, 1H), 2.40 (d, 1H), 1.96–0.94 (m, 23H) ppm.

Example 2b

Methyl (2R,3R)-2-Benzyl-3-hydroxyhexanoate

Diisopropylamine (8.61 mL, 65.7 mmol) is dissolved in 40 mL of anhydrous THF and chilled to 0° C. n-Butyllithium (30.1 mL of a 2.0M solution in hexanes, 60.2 mmol) is added dropwise over 10 min and the resulting pale yellow solution cooled to −78° C. A 15-mL THF solution of methyl (3R)-3-hydroxyhexanoate (4.00 g, 27.4 mmol) is added over 10 min and stirred for 30 min. Benzyl bromide (3.60 mL, 30.1 mmol) is dissolved in 12 mL of a 1:1 THF/HMPA solution and added at −78° C. dropwise. The resulting solution is allowed to warm slowly to 0° C. over 3 h. Aqueous 5% citric acid solution (250 mL) is added and the organics are extracted with two 250-mL portions of ether. The combined organics are washed with saturated aqueous sodium chloride. Drying over sodium sulfate and concentration is followed by which is chromatography on silica gel (elution with 25% EtOAc-hexanes) giving methyl (2R,3R)-2-benzyl-3-hydroxyhexanoate as an oil (3.03 g, 64% yield).

$^1$H NMR (300 MHz, CDCl$_3$) δ 7.30 (m, 2H), 7.18 (m, 3H), 3.65 (m, 1H), 3.62 (s, 3H), 3.02 (m, 2H), 2.75 (m, 1H), 2.55 (d, 1H), 1.50–1.35 (m, 4H), 0.90 (t, 3H) ppm.

Example 2c

Methyl (2R,3R)-2-Cyclohexylmethyl-3-hydroxyhexanoate

Methyl (2R,3R)-2-benzyl-3-hydroxyhexanoate (3.35 g, 14.2 mmol) is dissolved in 35 mL of MeOH. Under an argon atmosphere 1.00 g of 5% rhodium on carbon is added. The reaction vessel is evacuated and refilled with hydrogen several times and then pressurized with hydrogen to 65 psi. After 8 h the reaction vessel is evacuated and refilled with nitrogen. The solution is filtered and the filtrate concentrated in vacuo giving methyl (2R,3R)-2-cyclohexylmethyl-3-hydroxyhexanoate as an oil (3.44 g, 99% yield).

$^1$H NMR (300 MHz, CDCl$_3$) δ 3.72 (s, 3H), 3.65 (m, 1H), 2.60 (m, 1H), 2.40 (d, 1H), 1.96–0.94 (m, 23H) ppm.

Example 2d

(2R,3R)-2-Cyclohexylmethyl-3-hydroxyhexanoic Acid

Methyl (2R,3R)-2-cyclohexylmethyl-3-hydroxyhexanoate (3.44 g, 14.2 mmol) is dissolved in 3:1:1 THF-MeOH-H$_2$O (35 mL). To this is added lithium hydroxide monohydrate (1.79 g, 42.6 mmol). The reaction mixture is stirred for 18 h at 25° C. and the mixture is then extracted with ether. The aqueous layer is acidified with solid sodium bisulfate and then extracted with two 250-mL portions of ether. The combined organics are washed with saturated aqueous sodium chloride, dried over sodium sulfate, and concentrated under reduced pressure to afford (2R,3R)-2-cyclohexylmethyl-3-hydroxyhexanoic acid as a solid (3.05 g, 96% yield).

$^1$H NMR (300 MHz, CDCl$_3$) δ 3.67 (m, 1H), 2.60 (m, 1H), 1.85–0.94 (m, 20H) ppm.

Example 2e

(2R,3R)-2-Cyclohexylmethyl-3-hydroxyhexanoic Acid 2-Tetrahydropyranyloxyamide (2R,3R)-2-Cyclohexylmethyl-3-hydroxyhexanoic acid (3.00 g, 13.1 mmol) is dissolved in 30 mL of anhydrous dichloromethane. EDC (2.77 g, 14.5 mmol) is added followed by 2-tetrahydropyranyloxyamine (3.08 g, 26.3 mmol). The reaction is stirred at 25 ° C. for 8 h and is then poured into 200 mL of 1 M hydrochloric acid. The mixture is extracted with two 250-mL portions of dichloromethane. The combined organics are then washed with saturated aqueous sodium chloride, dried over sodium sulfate, and concentrated under reduced pressure to afford (2R,3R)-2-cyclohexylmethyl-3-hydroxyhexanoic acid 2-tetrahydropyranyloxyamide as a foam (3.60 g, 84% yield).

$^1$H NMR (300 MHz, CDCl$_3$) δ 8.45 (two s, 1H), 4.96 (two s, 1H), 3.95 (m, 1H), 3.64 (m, 2H), 2.75 (two d, 1H), 2.20 (m, 1H), 1.83–0.92 (m, 26H) ppm.

Example 2f

(3R,4S)-3-Cyclohexylmethyl-4-propyl-1-(2-tetrahydropyranyloxy)azetidin-2-one (2R,3R)-2-Cyclohexylmethyl-3-hydroxyhexanoic acid 2-tetrahydropyranyloxyamide (3.60 g, 11.0 mmol) is dissolved in 15 mL of pyridine and cooled to 0° C. Methanesulfonyl chloride (0.98 mL, 12.6 mmol) is added dropwise and the reaction is stirred at 0° C. for 6 h. The reaction is poured into 20 mL of ice cold 2 M hydrochloric acid and the mixture extracted with two 25-mL portions of EtOAc. The combined organics are washed with saturated aqueous sodium chloride solution, dried over sodium sulfate, and concentrated under reduced pressure to afford the methanesulfonate which is used with no further purification (4.00 g, 90% yield).

$^1$H NMR (300 MHz, CDCl$_3$) δ 8.34 and 8.27 (two s, 1H), 4.95 (m, 1H), 4.77 (m, 1H), 3.94 (m, 1H), 3.64 (m, 1H), 3.01 (s, 3H), 2.55 (m, 1H), 1.85–0.95 (m, 26H) ppm.

Potassium carbonate (4.09 g, 29.6 mmol) is added to 30 mL of acetone and the suspension is refluxed for 1 h. The above crude methanesulfonate (4.00 g, 9.86 mmol) is dissolved in 10 mL acetone and added. The resulting thick slurry continued to reflux for 16 h and is then cooled to 25° C. The mixture is filtered and the filtrate is concentrated under reduced pressure giving (3R,4S)-3-cyclohexylmethyl-4-propyl-1-(2-tetrahydropyranyloxy)azetidin-2-one as an oil (2.28 g, 75% yield).

$^1$H NMR (300 MHz, CDCl$_3$) δ 5.18 and 5.01 (two s, 1H), 4.23 and 4.14 (two m, 1H), 3.90 (m, 1H), 3.63 (m, 1H), 3.02 (m, 1H), 1.85–0.93 (m, 26H) ppm.

Example 2g

(2R,3S)-3-(2-Tetrahydropyranyloxyamino)-2-(cyclohexylmethyl)hexanoic Acid (3R,4S)-3-Cyclohexylmethyl-4-propyl-1-(2-tetrahydropyranyloxy)azetidin-2-one (2.25 g, 7.27 mmol) is dissolved in 10 mL of 1,4-dioxane. 2.5 N Aqueous sodium hydroxide solution (8.73 mL, 21.8 mmol) is added and the reaction stirred for 18 h at 25° C. The solution is diluted with 50 mL of ether and shaken. The organic phase is discarded and the aqueous layer is acidified with solid sodium bisulfate and then extracted with two 25-mL portions of ether. The combined organic phases are dried over sodium sulfate and concentrated in vacuo giving (2R,3S)-3-(2-tetrahydropyranyloxyamino)-2-(cyclohexylmethyl)hexanoic acid as an oil (2.02 g, 85% yield).

$^1$H NMR (300 MHz, CDCl$_3$) δ 4.84 and 4.74 (two s, 1H), 4.02 and 3.94 (two m, 1H), 3.60 (m, 1H), 3.16–3.03 and 2.91 (two m, 2H), 21.84–0.86 (m, 26H) ppm.

Example 2h

(2R,3S)-3-(Formyl-2-tetrahydropyranyloxyamino)-2-(cyclohexylmethyl)hexanoic Acid (2R,3S)-3-(2-Tetrahydropyranyloxyamino)-2-(cyclohexylmethyl)hexanoic acid (2.00 g, 6.11 mmol) is dissolved in 15 mL of pyridine. Formic acetic anhydride (1.08 mL, 12.2 mmol) is added at 25° C. The reaction is stirred for an additional 6 h and then is poured into 50 mL of cold 1 M hydrochloric acid. The organics are extracted with two 250-mL portions of dichloromethane. The combined organic phases are then washed with saturated aqueous sodium chloride, dried over sodium sulfate, and concentrated in vacuo to afford (2R,3S)-3-(formyl-2-tetrahydropyranyloxyamino)-2-(cyclohexylmethyl) hexanoic acid (2.17 g, 100% yield). APCI-MS m/z 378 (M+Na)$^+$, 354 (M−H)$^-$.

Example 2i

2R,3S)-3-(Formyl-2-tetrahydropyranyloxyamino)-2-(cyclohexylmethyl)hexanoic Acid [(1S)-4-(nitroimino-amino)methylamino-1-(1,3-thiazol-2-ylcarbamoyl)-1-butyl]amide To a 0° C. solution of (2R,3S)-3-(formyl-2-tetrahydropyranyloxyamino)-2-(cyclohexylmethyl)

hexanoic acid (114 mg, 0.321 mmol) in 1 mL of DMF is added diethyl cyanophosphonate (58 mg, 0.353 mmol) followed by NMM (33 mg). Stirring is continued for 30 min. at 0° C. (2S)-2-Amino-5-(nitroimino-amino) methylaminopentanoic acid 1,3-thiazol-2-ylamide hydrochloride (144 mg, 0.385 mmol) is added followed by additional NMM (97 mg). The mixture is heated at 40° C. for 16 h then is allowed to cool to 25° C. The reaction mixture is added to half-saturated aqueous sodium chloride and extracted with 1:1 EtOAc-ether. The combined organic layers are washed with pH 4.3 phosphate buffer, 5% aqueous sodium bicarbonate, saturated aqueous sodium chloride, and dried over magnesium sulfate. Concentration and purification by chromatography on silica gel (elution with 5% methanol in dichloromethane) provided 115 mg of (2R,3,S)-3-(formyl-2-tetrahydropyranyloxyamino)-2-(cyclohexylmethyl)hexanoic acid [(1S)-4-(nitroimino-amino)methylamino-1-(1,3-thiazol-2-ylcarbamoyl)-1-butyl]amide as a foam.

ESI-MS m/z 661 (MA+Na$^+$).

Example 2

(2R,3S)-3-(Formyl-hydroxyamino)-2-(cyclohexylmethyl)hexanoic Acid [(1S)-4-(Nitroimino-amino)methylamino-1-(1,3-thiazol-2-ylcarbamoyl)-1-butyl]amide (2R,3S)-3-(Formyl-2-tetrahydropyranyloxyamino)-2-(cyclohexylmethyl)hexanoic acid [(1S)-4-(nitroimino-amino)methylamino-1-(1,3-thiazol-2-ylcarbamoyl)-1-butyl]amide (115 mg, 0.180 mmol) is dissolved in 2 mL of 80% acetic acid and heated at 40° C. for 20 h. Concentration in vacuo and trituration with dichloromethane—ether provided 81 mg of (2R,3S)-3-(formyl-hydroxyamino)-2-(cyclohexylmethyl)hexanoic acid [(1S)-4-(nitroimino-amino)methylamino-1-(1,3-thiazol-2-ylcarbamoyl)-1-butyl]amide as a solid.

Mp 180° C. (dec) Anal: Calcd. for $C_{23}H_{38}N_8O_6S$ 0.25 $H_2O$: C, 49.40; H, 6.94; N, 20.04; S, 5.73. Found: C, 49.38; H, 6.96; N, 19.75; S, 5.57.

Example 3

(2R,3S)-3-(Formyl-hydroxyamino)-2-(2-methyl-1-propyl)butanoic Acid [(1S,2R)-2-Methyl-4-(nitroimino-amino)methylamino-1-(1,3-thiazol-2-ylcarbamoyl)-1-butyl]amide

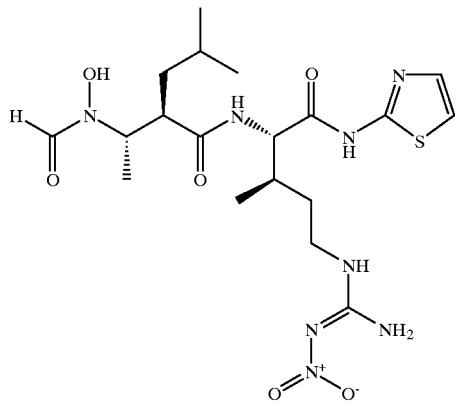

Example 3a

Methyl (2R,3R)-2-(2-Methyl-2-propen-1-yl)-3-hydroxybutanoate

A solution of 37.7 g (372 mmol) of diisopropylamine in 300 mL of THF is cooled to −40° C. and treated with 186.2 mL (372 mmol) of 2.0 M n-butyllithium in hexanes. The mixture is stirred at 0° C. for 15 min. The solution is then cooled to −78° C. and treated dropwise with 20 g (170 mmol) of methyl (3R)-3-hydroxybutyrate. This solution is stirred at 0° C. for 45 min, followed by stirring at −78° C. for 15 min. The flask is charged with 25.5 g (342 mmol) of 3-bromo-2-methyl-1-propene along with 15 mL of HMPA and stirred for 4 h at −78° C. The reaction mixture then is allowed to stand at −20° C. for 19 h. The reaction is slowly treated with excess saturated aqueous ammonium chloride over 15 min and the resulting solution is partitioned between ether and 1 N aqueous hydrochloric acid. The organics are dried over magnesium sulfate and concentrated in vacuo to afford 23.1 g of crude oil. A sample (10 g) of the crude product is chromatographed on silica gel (elution with 4:1 hexanes-EtOAc) to afford 8.1 g (28%) of methyl (2R,3R)-2-(2-methyl-3-propen-1-yl)-3-hydroxybutanoate as an oil.

$^1$H NMR (400 MHz, CDCl$_3$) δ 4.77 (d, 2H), 3.90 (m, 1H), 3.69 (s, 3H), 2.68 (m, 1H), 2.52–2.41 (m, 2H), 2.36 (m, 1H), 1.5 (s, 3H), 1.22 (s, 3H) ppm. APCI-MS m/z 173 (M+H)$^+$.

Example 3b

Methyl (2R,3R)-2-(2-Methyl-1-propyl)-3-hydroxybutanoate

Methyl (2R,3R)-2-(2-methyl-2-propen-1-yl)-3-hydroxybutanoate (8.1 g, 47.1 mmol) in 85 mL of EtOAc is treated with 800 mg of 10% palladium on carbon and the mixture is evacuated and purged with nitrogen. The heterogeneous solution is stirred under 52 psi of hydrogen for 1.5 h. Filtration and concentration of the filtrate in vacuo affords 7.99 g (96%) of methyl (2R,3R)-2-(2-methyl-1-propyl)-3-hydroxybutanoate as an oil.

$^1$H NMR (400 MHz, CDCl$_3$) δ 3.85 (m, 1H), 3.69 (s, 3H), 2.51–2.42 (m, 2H), 1.71–1.62 (m, 1H), 1.58–1.48 (m, 1H), 1.38–1.30 (m, 1H), 1.22 (d, 3H), 0.94–0.86 (dd, 6H) ppm. APCI-MS m/z 175 (M+H)$^+$.

Example 3c (2R,3R)-2-(2-Methyl-1-propyl)-3-hydroxybutanoic Acid

Methyl (2R,3R)-2-(2-methyl-1-propyl)-3-hydroxybutanoate (7.99 g, 46 mmol) in 50 mL of THF is treated with 50 mL of water containing 3.9 g (92 mmol) of lithium hydroxide monohydrate. The reaction flask is treated with 5.0 mL of MeOH and allowed to stir for 17 h at 25° C. The mixture is partitioned between water and ether followed by separation of the aqueous layer. The aqueous solution is brought to pH 3 with 6 N aqueous hydrochloric acid and the mixture is extracted with ether. The organic phase is dried over magnesium sulfate and concentrated under reduced pressure to afford 6.6 g (90%) of (2R,3R)-2-(2-methyl-1-propyl)-3-hydroxybutanoic acid.

$^1$H NMR (400 MHz, CDCl$_3$) δ 3.91 (m, 1H), 2.50 (m, 1H), 1.75–1.61 (m, 2H), 1.40–1.29 (m, 1H), 1.29–1.24 (d, 3H), 0.96 (dd, 6H) ppm. APCI-MS m/z 161 (M+H)$^+$.

Example 3d (2R,3R)-2-(2-Methyl-1-propyl)-3-hydroxyhexanoic Acid 2-Tetrahydropyranyloxyamide (2R,3R)-2-(2-Methyl-1-propyl)-3-hydroxybutanoic acid (6.6 g, 41.2 mmol) and 5.3 g (45.3 mmol) of 2-tetrahydropyranyloxyamine are stirred in 60 mL of dichloromethane as 8.7 g (45.3 mmol) of EDC is added. After 4 h at 25° C. the reaction mixture is partitioned between 1 N aqueous hydrochloric acid and dichloromethane and the organics are washed with saturated aqueous sodium bicarbonate. The organics are dried over magnesium sulfate and concentrated under reduced pressure to afford 5.9 g (55%) of (2R,3R)-2-(2-methyl-1-propyl)-3-hydroxyhexanoic acid 2-tetrahydropyranyloxyamide as an oil.

$^1$H NMR (400 MHz, CDCl$_3$) δ 8.45 (d, 1H), 5.0 (d, 1H), 3.81–4.00 (m, 2H), 2.05–2.15 (m, 1H), 1.45–1.83 (m, 10H), 1.23–1.38 (m, 1H), 1.22 (d, 3H), 0.96 (dd, 6H) ppm. APCI-MS m/z 260 (M+H)$^+$.

Example 3e (3R,4S)-3-(2-Methyl-1-propyl)-4-methyl-1-(2-tetrahydropyranyloxy)azetidin-2-one (2R,3R)-2-(2-Methyl-1-propyl)-3-hydroxyhexanoic acid 2-tetrahydropyranyloxyamide (5.8 g, 22.3 mmol) in 42 mL of dry pyridine is cooled to 0° C. and treated with 2.81 g (24.6 mmol) of methanesulfonyl chloride followed by stirring at 0° C. for 4 h. The reaction mixture is poured into 1 N aqueous hydrochloric acid and extracted with EtOAc. The organics are washed with three portions of saturated aqueous cupric sulfate. The organic layer is dried over magnesium sulfate and concentrated under reduced pressure to provide 6.1 g of the crude methanesulfonate which is used directly in the next step.

The crude methanesulfonate is stirred in 150 mL of dry acetone and treated with 7.5 g (54.3 mmol) of potassium carbonate. The reaction is stirred at reflux for 17 h and the mixture is then allowed to cool to 25° C. The mixture is filtered and the filtrate is concentrated to afford an oil (4.5 g) which is chromatographed on silica gel (elution with 4:1 hexanes-EtOAc) to give 3.5 g (65%) of (3R,4S)-3-(2-methyl-1-propyl)-4-methyl-1-(2-tetrahydropyranyloxy) azetidin-2-one as an oil.

$^1$H NMR (400 MHz, CDCl$_3$) δ 5.10 and 4.97 (two m, 1H), 4.18–3.97 (m, 2H), 3.60 (m, 1H), 3.03–2.88 (m, 1H), 1.82–1.50 (m, 8H), 1.30–1.25 (m, 1H), 1.24–1.20 (dd, 3H), 0.95 (dd, 6H) ppm. APCI-MS m/z 242 (M+H)$^+$.

Example 3f (2R,3S)-3-(2-Tetrahydropyranyloxyamino)-2-(2-methyl-1-propyl)butanoic Acid (3R,4S)-3-(2-Methyl-1-propyl)-4-methyl-1-(2-tetrahydropyranyloxy)azetidin-2-one (3.5 g, 14.5 mmol) in 30 mL of ethylene glycol dimethyl ether is treated with 20 mL of 2.5 M aqueous sodium hydroxide solution. The mixture is stirred at 25° C. for 16 h and is then brought to pH 3 by addition of saturated aqueous sodium bisulfate solution. The mixture is extracted with ether and the organics are dried over magnesium sulfate and concentrated under reduced pressure to give 3.2 g (84%) of (2R,3S)-3-(2-tetrahydropyranyloxyamino)-2-(2-methyl-1-propyl) butanoic acid as an oil.

$^1$H NMR (400 MHz, CDCl$_3$) δ 4.82 and 4.74 (two m, 1H), 4.00–3.83 (m, 1H), 3.60–3.50 (m, 1), 3.33–3.20 (m, 1H), 3.00–2.96 (m, 1H), 1.82–1.40 (m, 8H), 1.20–1.08 (m, 1H), 1.11–1.05 (dd, 3H), 0.93 (dd, 6H) ppm. APCI-MS m/z 260 (M+H)$^+$.

Example 3g

N-Trifluoroacetylglycine

A suspension of 100 g (1.33 mol) of glycine in 450 mL of TFA is treated with 385 mL (2.73 mol) of trifluoroacetic anhydride. The mixture is allowed to stir for 1.5 h. The mixture is concentrated in vacuo and is treated with 1 L of 1:1 chloroform-hexanes. The slurry is concentrated in vacuo, treated with 1 L of EtOAc, warmed, then allowed to cool to 25° C. and then to 4° C. The solid is collected and dried to afford 89.21 g of N-trifluoroacetylglycine as a solid. The filtrate is concentrated in vacuo, treated with EtOAc, warmed, and allowed to cool to 25° C. Collection of the solid affords a further 58.08 g of N-trifluoroacetylglycine.

$^1$H NMR (400 MHz, CDCl$_3$) δ 12.90 (s, 1H), 9.75 (s, 1H), 3.81 (s, 2H) ppm.

Example 3h (2E)-2-Buten-1-yl N-Trifluoroacetylglycinate

A mixture of 143.1 g (836 mmol) of N-trifluoroacetylglycine in 1 L of DMF is chilled to −8° C. as 100 mL (844 mmol) of E-crotyl bromide is added dropwise, followed by addition of 140 mL (937 mmol) of DBU at −5° C. After 1.5 h at −5° C. and 2 h at −2° C. the mixture is allowed to warm to 25° C. The mixture is cooled to 0° C. and 40 mL more DBU is added. After warming to 25° C. the mixture is concentrated in vacuo. 1 L of 1:1 ether-water is added. The organic layer is separated, washed with water, 1 N HCl, saturated aqueous sodium bicarbonate, and saturated aqueous sodium chloride. Drying and concentration in vacuo is followed by trituration of the oil with hexanes-EtOAC to provide a solid. Chromatography on silica gel (elution with 3:1 hexanes-EtOAc) affords 49.96 g of (2E)-2-buten-1-yl N-trifluoroacetylglycinate as an oil.

$^1$H NMR (400 MHz, d$_6$-DMSO) δ 9.87 (bs, 1H), 5.75 (m, 1H), 5.55 (m, 1H), 4.51 (d, 2H), 3.96 (d, 2H), 1.64 (d, 3H) ppm.

Example 3i (2S,3R)-2-Trifluoroacetylamino-3-methyl-4-pentenoic Acid

A solution of 217 mL (1.04 mol) of hexamethyldisilazane in 400 mL of THF is chilled to −28° C. and treated with 400 mL (1.0 mol) of 2.5 M n-butyllithium in hexanes. This solution of lithium hexamethyldisilazide is allowed to warm to 25° C. and is then added dropwise to a −78° C. mixture of 45 g (0.20 mol) of (2 E)-2-buten-1-yl N-trifluoroacetylglycinate, 45 g (0.220 mol) of aluminum triisopropoxide, and 162 g (0.50 mol) of dry quinidine in 1400 mL of THF. The mixture is stirred at −77° C. for 1 h, then is allowed to warm to 25° C. After 2 d the mixture is treated with 300 mL of ether and 2 L of 1.25 M aqueous potassium bisulfate. Additional solid bisulfate is added to adjust pH to 2. The organic phase is separated and the aqueous phase is extracted with ether. The combined organic phases are washed with aqueous potassium bisulfate, then extracted with 10% aqueous sodium bicarbonate. The aqueous phase is carefully acidified with solid sodium bisulfate to pH 1, then the mixture is extracted with ether. Addition of charcoal to the organic phase, drying over magnesium sulfate, filtration, and concentration in vacuo affords 25.16 g (56%) of (2S,3R)-2-trifluoroacetylamino-3-methyl-4-pentenoic acid as an oil.

$^1$H NMR (300 MHz, CDCl$_3$) δ 9.82 (bs, 1H), 6.78 (bd, 1H), 5.72 (ddd, 1H), 5.19 (m, 2H), 4.68 (dd, 1H), 2.84 (m, 1H), 1.17 (d, 3H) ppm.

Example 3j (2S,3R)-2-Benzyloxycarbonylamino-3-methyl-4-pentenoic Acid

A mixture of 25.16 g (112 mmol) of (2S,3R)-2-trifluoroacetylamino-3-methyl-4-pentenoic acid and 112 mL of 2 N aqueous sodium hydroxide is stirred at 80° C. for 1.5 h. The mixture is then allowed to cool to 25° C. and is further chilled to 0° C. 2 N aqueous sodium hydroxide (112 mL) is added followed by dropwise addition of 18 mL (126 mmol) of benzyl chloroformate. After 45 min at 0° C. and 5 h at 25° C. the mixture is added to 150 mL of water and is treated with aqueous sodium hydroxide until an orange solution resulted. The mixture is extracted with ether. The aqueous phase is acidified with 6 N HCl to pH 1 and is extracted with ether. Drying over magnesium sulfate and concentration in vacuo affords 22.61 g (77%) of (2S,3R)-2-benzyloxycarbonylamino-3-methyl-4-pentenoic acid as an oil.

$^1$H NMR (300 MHz, CDCl$_3$) δ 8.39 (bs, 1H), 7.35 (bs, 5H), 5.71 (ddd, 1H), 5.13 (m, 2H), 4.43 (dd, 1H), 2.74 (m, 1H), 1.10 (d, 3H) ppm. ESI-MS m/z 264 (M+H)$^+$, 286 (M+Na)$^+$.

Example 3k tert-Butyl (2S,3R)-2-Benzyloxycarbonylamino-3-methyl4-pentenoate

A solution of 20.6 g (78.2 mmol) of (2S,3R)-2-benzyloxycarbonylamino-3-methyl-4-pentenoic acid in 156 mL of toluene is heated to 80° C. as 75 mL (313 mmol) of dimethylformamide di-tert-butyl acetal is added. After 45 min at 80° C. an additional 10 mL of dimethylformamide di-tert-butyl acetal is added and the mixture is allowed to stir at 80° C. for 1 h. The mixture is cooled to 25° C. and ether is added. The mixture is washed with water, 5% aqueous sodium bicarbonate, saturated aqueous sodium chloride, and is dried over magnesium sulfate. Concentration in vacuo gives 15.49 g (62%) of tert-butyl (2S,3R)-2-benzyloxycarbonylamino-3-methyl-4-pentenoate as an oil.

$^1$H NMR (300 MHz, CDCl$_3$) δ 7.30 (m, 5H), 5.75 (m, 1H), 5.28 (bd, 1H), 5.07 (m, 2H), 4.27 (bd, 1H), 2.63 (m, 1H), 1.44 (s, 9H), 1.04 (d, 3H) ppm.

Example 3l tert-Butyl (2S,3R)-2-benzyloxycarbonylamino-3-methyl-5-hydroxypentanoate To a 0° C. solution of 2,3-dimethyl-2-butene in THF (43.2 mmol, 1.0 M) is added a solution of borane in THF (43.2 mmol, 1.0 M) dropwise over 20 min. After stirring an additional 60 min at 0° C., tert-butyl (2S,3R)-2-benzyloxycarbonylamino-3-methyl-4-pentenoate (13.15 g, 41.2 mmol) in 20 mL THF is added dropwise, and the resulting solution is allowed to come to 25° C. over 60 min. The solution is cooled again to 0° C. and quenched with 6 ml of 1:1 THF-ethanol, added cautiously, then 40 mL of pH 7.0 phosphate buffer. 40 mL 30% hydrogen peroxide is added and the reaction mixture is stirred at 25° C. for 14 h. The mixture is partially concentrated, added to saturated aqueous sodium chloride, and extracted with ether. The combined organic layers are washed twice with ice-cold saturated aqueous sodium sulfite, water, and saturated aqueous sodium chloride, and dried over magnesium sulfate. Concentration in vacuo and purification by silica gel chromatography (elution with hexanes-EtOAc, 3:2) provides tert-butyl (2S,3R)-2-benzyloxycarbonylamino-3-methyl-5-hydroxypentanoate as an oil (12.3 g, 89%).

ESI-MS m/z 360 (M+Na)$^+$ 338 (M+H)$^+$ $^1$H NMR (CDCl$_3$, 400 MHz) δ 7.34 (m, 5H), 5.40 (bd, 1H), 5.09 (s, 2H), 4.11 (m, 1H), 3.78 (m, 1H), 3.65 (m, 2H), 2.22 (m, 1H), 1–7–1.6 (bs, 1H), 1.63 (m, 2H), 1.45 (s, 9H), 0.84 (d, 3H) ppm.

Example 3m tert-Butyl (2S,3R)-2-Benzyloxycarbonylamino-3-methyl-5-azidopentanoate tert-Butyl (2S,3R)-2-benzyloxycarbonylamino-3-methyl-5-hydroxypentanoate (12.3 g, 36.4 mmol) is dissolved in 60 mL dichloromethane and 8.8 mL pyridine and cooled to 0° C. Methanesulfonyl chloride (4.59 g, 40.1 mmol, 3.10 mL) is added via syringe and the resulting solution allowed to stir for 14 h. The reaction mixture is washed with 1 N HCl, saturated aqueous sodium chloride, and is dried over magnesium sulfate. Filtration and concentration provides the crude methanesulfonate which is taken up in 50 mL of DMF and heated at 50° C. with LiN$_3$ (5.36 g, 109 mmol) for 3 h. The reaction mixture is added to water and extracted three times with ether. The combined extracts are dried over magnesium sulfate and concentrated to give the crude azide (10.3 g) which is purified by chromatography on silica gel (hexanes-EtOAc 8:1) to give tert-butyl (2S,3R)-2-benzyloxycarbonylamino-3-methyl-5-azidopentanoate as an oil (9.40 g, 71%).

$^1$H NMR (CDCl$_3$, 400 MHz) δ 7.34 (m, 5H), 5.28 (bd, 1H), 5.09 (s, 2H), 4.31 (m, 1H), 3.39 (m, 2H), 2.18 (m, 1H), 1.72 (m, 1H), 1.45 (s, 9H), 1.44 (m, 1H), 1.84 (d, 3H) ppm. ESI-MS m/z 385 (M+Na)$^+$, 329 (M+Na-C$_4$H$_8$)$^+$.

Example 3n tert-Butyl (2S,3R)-2-Benzyloxycarbonylamino-3-methyl-5-(imino-amino) methylammoniumpentanoate Nitrate tert-Butyl (2S,3R)-2-benzyloxycarbonylamino-3-methyl-5-azidopentanoate (1.02 g, 2.81 mmol) and TEA (0.39 mL, 2.8 mmol) are dissolved in 10 mL methanol and hydrogenated at 30 psi over 0.05 g of Lindlar catalyst. After 4 h, the catalyst is filtered and the filtrate concentrated to give the primary amine as a clear oil (940 mg, 100%). The amine (906 mg, 2.69 mmol) is immediately taken up in 5 mL of DMF and a solution of 3,5-dimethylpyrazole-1-carboxamidine nitrate (542 mg, 2.69 mmol) and TEA (0.4 mL) in 5 mL DMF is added followed by an additional 0.4 mL of TEA. After 3 d at 25° C., volatiles are removed under vacuum and the resulting residue triturated with EtOAc (40 mL) and sonicated to a fine suspension. The solid is collected and washed with EtOAc to provide 856 mg (72%) of tert-butyl (2S,3R)-2-benzyloxycarbonylamino-3-methyl-5-(imino-amino)methylammoniumpentanoate nitrate as a glassy solid.

ESI-MS m/z 379(M+H)$^+$, 323 (M+H—C$_4$H$_8$)$^+$; $^1$H NMR (DMSO-d$_6$, 400 MHz) δ 7.53 (bd, 1H), 7.45 (bs, 1H), 7.33 (m, 5H), 7.4–6.5 (bs, 2H), 5.02 (m, 2H), 4.00 (m, 1H), 3.05 (m, 4H), 1.98 (m, 1H), 1.6–1.1 (m, 2H), 1.37 (s, 9H), 0.82 (bs, 3H) ppm.

Example 3o tert-Butyl (2S,3R)-2-amino-3-methyl-5-(imino amino)methylammoniumpentanoate Nitrate tert-Butyl (2S,3R)-2-benzyloxycarbonylamino-3-methyl-5-(imino-amino)methylammoniumpentanoate nitrate (856 mg, 1.94 mmol) is dissolved in 10 mL methanol and 2 mL of 1,4-cyclohexadiene. 10% Palladium on carbon (80 mg) is added and the mixture is refluxed for 60 min. The warm solution is filtered and the filtrate is concentrated in vacuo to give tert-butyl (2S,3R)-2-amino-3-methyl-5-(imino-amino)methylammoniumpentanoate nitrate as a glass (599 mg, 100%).

ESI-MS m/z 245 (M+H)+.

Example 3p (2S,3R)-2-tert-Butoxycarbonylamino-3-methyl-5-(nitroimino-amino)methylaminopentanoic Acid tert-Butyl (2S,3R)-2-amino-3-methyl-5-(imino-amino)methylammoniumpentanoate nitrate (599 mg) is taken up in 95% TFA. After 6 h, the TFA is stripped and the resulting residue repeatedly stripped from ethanol, EtOAc, isopropanol then finally toluene to provide (2S,3R)-2-amino-3-methyl-5-(imino-amino)methylammoniumpentanoic acid nitrate trifluoroacetate as an oil (1.04 g).

ESI-MS m/z 189 (M+H)+ 172 (M+H—NH$_3$)+.

(2S,3R)-2-amino-3-methyl-5-(imino-amino)methylammoniumpentanoic acid nitrate trifluoroacetate (1.04 g) is dissolved in 1 mL concentrated H$_2$SO$_4$ and cooled in an ice/acetone bath with stirring. A precooled (−15° C.) mixture of fuming sulfuric acid (2.5 mL) and fuming nitric acid (1.7 mL) is added and the thick mixture is stirred for 2 h at −10 to −15° C. Ice is added followed by the cautious addition of concentrated NH$_4$OH to pH 8. The mixture is then acidified to pH 5 with acetic acid. Volatiles are removed in vacuo to provides a yellow solid which is triturated for 1 h in methanol then sonicated for 10 min. Filtration through glass provides the product as a yellow solid contaminated with NH$_4$Cl (ESI-MS m/z 234 (M+H)+). The crude (2S,3R)-2-amino-3-methyl-5-(nitroimino-amino)methylaminopentanoic acid is dissolved in 15 mL of 5% sodium bicarbonate, concentrated to dryness, then taken up again in 10 mL of 5% sodium bicarbonate. THF (10 mL) is added, followed by di-tert-butyl dicarbonate (465 mg, 2.13 mmol). After stirring for 18 h, additional sodium bicarbonate (5 g) and di-tert-butyl dicarbonate (50 mg) is added. After 4 d the reaction mixture is extracted with ether, acidified to pH 1 with 6 N HCl, then extracted with dichloromethane, saturated with solid sodium chloride, then extracted further with dichloromethane. The combined dichloromethane layers are washed with saturated aqueous sodium chloride, dried over magnesium sulfate, and concentrated in vacuo to provide crude (2S,3R)-2-tert-butoxycarbonylamino-3-methyl-5-(nitroimino-amino)methylaminopentanoic acid (125 mg).

ESI-MS m/z 356 (M+Na)+ 334 (M+H)+ 278 (M+H—C$_4$H$_8$)+; $^1$H NMR (CDCl$_3$, 400 MHz) δ 11.0–10.5 (bs, 2H), 8.68 (bs, 1H), 87.9–7.5 (bs, 1H), 5.39 (d, 1H), 4.45 (d, 1H), 3.69 (m, 1H), 3.29 (m, 1H), 2.18 (m, 1H), 1.62 (m, 1H), 1.48 (m, 1H), 1.44 (s, 9H), 0.86 (d, 3H) ppm.

Example 3q (2S,3R)-2-tert-Butoxycarbonylamino-3-methyl-5-(nitroimino-amino)methylaminopentanoic Acid 1,3-Thiazol-2-ylamide (2S,3R)-2-tert-Butoxycarbonylamino-3-methyl-5-(nitroimino-amino)methylaminopentanoic acid (123 mg, 0.396 mmol) is dissolved in 1 mL of DMF and cooled to −23° C. TEA (51 μL, 0.37 mmol) is added followed by isobutyl chloroformate (48 μL, 0.37 mmol). After 40 min, 2-aminothiazole is added and the reaction mixture is allowed to come to 25° C. over 18 h. The reaction mixture is added to half-saturated aqueous sodium chloride and extracted with EtOAc. The combined organic layers are washed with 1N HCl, 5% sodium bicarbonate, saturated aqueous sodium chloride, and dried over magnesium sulfate. Concentration in vacuo and purification by chromatography on silica gel (elution with hexanes-EtOAc 1:5 then EtOAc) provides (2S,3R)-2-tert-butoxycarbonylamino-3-methyl-5-(nitroimino-amino)methylaminopentanoic acid 1,3-thiazol-2-ylamide as a foam (101 mg, 66%).

ESI-MS m/z 416 (M+H)+ 360 (M+H—C$_4$H$_8$)+; $^1$H NMR (CD$_3$OD, 400 MHz) δ 7.35 (d, 1H), 7.03 (d, 1H), 6.85 (bd, 1H), 4.31 (m, 1H), 3.27 (m, 2H), 2.04 (m, 1H), 1.62 (m, 1H), 1.44–1.27 (m, 2H), 1.36 (s, 9H), 0.86 (d, 3H) ppm.

Example 3r (2S,3R)-2-Amino-3-methyl-5-(nitroimino-amino)methylaminopentanoic Acid 1,3-Thiazol-2-ylamide Hydrochloride (2S,3R)-2-tert-Butoxycarbonylamino-3-methyl-5-(nitroimino-amino)methylaminopentanoic acid 1,3-thiazol-2-ylamide (101 mg, 0.243 mmol) is dissolved in 1 mL THF and 1.5 mL of 4 N HCl in dioxane is added. After 2 h, THF is added and the white precipitate is collected by filtration. The resulting oily solid is treated with methanol and concentrated in vacuo. THF is added and the mixture is concentrated in vacuo; this THF addition and concentration is repeated several times to give (2S,3R)-2-amino-3-methyl-5-(nitroimino-amino)methylaminopentanoic acid 1,3-thiazol-2-ylamide hydrochloride as a solid (83 mmol, 97%).

ESI-MS m/z 338 (M+Na)+ 316 (M+H)+.

Example 3

(2R,3S)-3-(Formyl-hydroxyamino)-2-(2-methyl-1-propyl)butanoic Acid [(1S, 2R)-2-Methyl-4-(nitroimino-amino)methylamino-1-(1,3-thiazol-2-ylcarbamoyl)-1-butyl]amide To a 0° C. solution of (2R,3S)-3-(formyl-2-tetrahydropyranyloxyamino)-2-(2-methyl-1-propyl)butanoic acid (34 mg, 0.12 mmol) in 1 mL anhydrous DMF is added diethyl cyanophosphonate (19 mg, 0.119 mmol) followed by NMM (12 mg). Stirring is continued for 30 min at 0° C. (2S,3R)-2-Amino-3-methyl-5-(nitroimino-amino)methylaminopentanoic acid 1,3-thiazol-2-ylamide hydrochloride (42 mg, 0.119 mmol) is added followed by additional NMM (36 mg). The mixture is heated at 40° C. for 16 h then allowed to cool to 25° C. The reaction mixture is added to half-saturated aqueous sodium chloride and extracted with 1:1 EtOAc-ether. The combined organic layers are washed with pH 4.3 phosphate buffer, 5% aqueous sodium bicarbonate, saturated aqueous sodium chloride, and dried over magnesium sulfate. Concentration and chromatography on silica gel (elution with 5% methanol in dichloromethane) provides 35 mg of (2R,3S)-3-(formyl-tetrahydropyranyloxyamino)-2-(2-methyl-1-propyl)butanoic acid [(1S,2R)-2-methyl-4-(nitroimino-amino)methylamino-1-(1,3-thiazol-2-ylcarbamoyl)-1-butyl]amide as a foam.

ESI-MS m/z 607 (M+Na)+.

(2R,3S)-3-(Formyl-tetrahydropyranyloxyamino)-2-(2-methyl-1-propyl)butanoic acid [(1S,2R)-2-methyl-4-(nitroimino-amino)methylamino-1-(1,3-thiazol-2-ylcarbamoyl)-1-butyl]amide (30 mg, 0.049 mmol) is dissolved in 2 mL of 80% acetic acid and heated at 40° C. for 20 h. Concentration in vacuo, trituration with dichloromethane/ether, and collection of the product provides 26 mg of (2R,3S)-3-(formyl-hydroxyamino)-2-(2-methyl-1-propyl)butanoic acid [(1S,2R)-2-methyl-4-(nitroimino-amino)methylamino-1-(1,3-thiazol-2-ylcarbamoyl)-1-butyl]amide as a solid.

ESI-MS m/z 501 (M+H)$^+$; Anal. Calcd. For $C_{19}H_{32}N_8O_6S$ 0.75$H_2O$: C, 44.39; H, 6.57; N, 21.80; Found: C, 44.46; H, 6.39; N, 21.48.

PHARMACOLOGY

The efficacy of compounds of the present invention as inhibitors of matrix metalloproteases, TNFα converting enzyme and TNFα cellular release can be evaluated and measured using pharmacological methods known in the art or as described in detail below based on similarly established methodologies.

Pharmacological Example 1

A. Matrix Metalloprotease Inhibition Protocol

The potency of compounds of the invention as inhibitors of 19 kD truncated collagenase-1 (MMP-1), 20 kD truncated collagenase-3 (MP-13), stromelysin-1 (MP-3), and 50 kD truncated gelatinase B MMP-9) is determined according to the general procedure of Bickett et. al. (*Anal Biochem.* 1993, 212, 58–64) using the fluorogenic substrate, DNP-Pro-Cha-Gly-Cys(Me)-His-Ala-Lys(NMA)-NH$_2$ (DNP=2,4-dinitrophenyl, NMA=N-methylanthranilic acid). Assays are conducted in a total volume of 0.180 mL assay buffer (200 mM NaCl, 50 mM Tris, 5 mM $CaCl_2$, 10 μM $ZnSO_4$, 0.005% Brij 35, pH 7.6) in each well of a black 96-well microtiter plate. 19 kD collagenase-1, 20 kD collagenase-3, stromelysin-1, and 50 kD gelatinase B concentrations are adjusted to 500 pM, 30 pM, 5 nM, and 100 pM, respectively. A dose response is generated using an eleven-point, 3-fold serial dilution with initial starting test compound concentrations of 100, 10, or 1 μM. Inhibitor and enzyme reactions are incubated for 30 minutes at ambient temperature and then initiated with 10 μM fluorogenic substrate (above). The product formation is measured at Excitation$_{343}$/Emission$_{450}$ nm after 45–180 minutes using a Fluostar SLT fluorescence analyzer. Percent inhibition is calculated at each inhibitor concentration and the data are plotted using standard curve fitting programs. IC$_{50}$ values are determined from these curves. Assays are run at low substrate concentration ([S]<<K$_m$) such that the calculated IC$_{50}$ values are equivalent to K$_i$ within experimental error.

B. TNFα Converting Enzyme Inhibition Protocol

The potency of compounds of the invention as inhibitors of cell—free tumor necrosis factor α converting enzyme is determined as follows; Membrane preparation from Mono-Mac 6 cells (subfractionated extract from equivalent of 6×10$^6$ cells per 60 μl assay) is incubated for 1 hr with 200 nM radiolabeled substrate (Biotin-SPLAQAVRSSSRT-($^3$H)P-S-NH$_2$, 4.1 Ci/mmol, ref #0935 from Zeneca) in 10 mM hepes buffer, 250 mM sucrose, pH 7.5. The reaction is quenched by addition of streptavidin SPA beads (Amersham RPNQ0006), with excess binding capacity relative to substrate, suspended in 250 mM EDTA, pH 8.0. Binding is complete within 15 minutes and plates are counted in a Wallac 1450 Microbeta liquid scintillation counter. Percent inhibition is calculated at each inhibitor concentration and the data are plotted using standard curve fitting programs. IC$_{50}$ values are determined from these curves. Assays are run at low substrate concentration ([S]<<K$_m$) such that the calculated IC$_{50}$ values are equivalent to K$_i$ within experimental error.

C. Cell—Based TNFα Release Inhibition Protocol

The potency of compounds of the invention as inhibitors of release of soluble tumor necrosis factor α from stimulated monocytes in vitro is determined as follows; LPS/PMA solution for assay consisting of a) 4 μL of 5 mg/mL LPS stock and b) 6 μL of 10 mg/mL PMA stock are added to 500 μL of medium (RPMI+10% FBS+penicillin/streptomycin+1-glutamine). This solution is then diluted 1:1000 (40 ng/mL and 120 ng/mL) for use later in the assay. Compounds (10 mM) are serially diluted 1:3 in DMSO. Compound dilutions (20 μL) are added to a sterile round bottom 96 well plate (20 μL:200 μL total volume=1:10 for final concentrations of 50 μM for test compounds). MonoMac 6 cell suspension (130 μL, 1.5×10$^6$ cells/mL) is then added to each well resulting in 2×10$^5$ cells/well. LPS/PMA (50 μL) solution is then added to each well (final concentrations of 10 ng/mL and 30 ng/mL respectively). The plate is incubated at 37° C. for 2 h then spun at 1,500 rpm for 3 min to pellet cells. The supernatant (120 μL/well) is removed to a new round bottom 96 well plate and diluted 1:10 in PBS. Then, 20 μL of the supernatant is transferred to a Cistron TNFβ ELISA plate and processed according to the manufacturer's instructions to quantitate levels of TNFα. Percent inhibition of TNFα release is calculated at each inhibitor concentration and the data are plotted using standard curve fitting programs. IC$_{50}$ values are determined from these curves.

Results are listed in Table 3.

TABLE 3

| Example | TNFα Converting Enzyme K$_i$ | Collagenase-1 K$_i$ | Collagenase-3 K$_i$ | Gelatinase B K$_i$ | Stromelysin-1 K$_i$ | TNFα Release Inhibition IC$_{50}$ |
|---|---|---|---|---|---|---|
| Example 1 | + | + | + | + | + | + |
| Example 2 | + | ++ | + | + | ++ | + |
| Example 3 | + | + | + | + | ++ | + |
| Example 4 | + | + | nd | + | ++ | + |
| Example 5 | + | + | + | + | + | +++ |
| Example 6 | + | ++ | + | + | ++ | ++ |
| Example 7 | + | ++ | + | ++ | ++ | ++ |

TABLE 3-continued

| Example 8 | + | ++ | + | + | ++ | + |
| Example 9 | + | +++++ | + | ++ | ++ | ++ |
| Example 10 | + | ++ | ++ | +++ | +++++ | +++ |

| Key; | + | <50 nM |
| | ++ | 50 nM–250 nM |
| | +++ | 250 nM–500 nM |
| | ++++ | 500 nM–1 μM |
| | +++++ | >1 μM |
| | nd | not done |

Pharmacological Example 2
Murine LPS—Stimulated Serum TNF Inhibition Protocol

The potency of compounds of the invention as inhibitors of serum TNFα elevation in mice treated with lipopolysaccharide (LPS) is determined as follows; a) for subcutaneous (s.c.) administration, test compound is dissolved in DMSO and added to a mixture of 0.9% sodium chloride solution and 30% Trappsol HPB-20 (Cyclodextrin Technology Development Inc., Gainesville, Fla. USA) for a final DMSO concentration of 1%. The dosing solution is sonicated briefly and 0.2 mL is injected subcutaneously 10 min prior to LPS injection, b) for per oral (p.o.) administration, test compounds are formulated in 0.2 mL of PBS and 0.1% Tween 80 and given orally via gavage 10 min prior to LPS administration.

C3/hen female mice are injected intraperitoneally with 200 μg/kg LPS (*Escherichia coli*, Serotype 0111:B4, Sigma Chemical Co, St. Louis, Mo.) in PBS and sacrificed 90 min later by CO$_2$ asphyxiation. Blood is immediately taken from the caudal vena cava and plasma prepared and frozen at –80° C. Plasma concentrations of TNF are measured by ELISA (Genzyme Co., Cambridge Mass.).

Results are listed in Table 4.

TABLE 4

| Compound | Route of Administration | Dose | Percentage Inhibition of Serum TNFα |
|---|---|---|---|
| Example 1 | s.c. | 40 mg/kg | +++ |
| Example 2 | s.c. | 40 mg/kg | ++ |
| Example 6 | s.c. | 40 mg/kg | ++ |
| Example 7 | s.c. | 40 mg/kg | ++ |
| Example 8 | s.c. | 40 mg/kg | ++ |
| Example 10 | s.c. | 40 mg/kg | ++ |

| Key: | + | 25%–50% |
| | ++ | 50%–75% |
| | +++ | >75% |

Throughout this application, various publications are referenced. These publications are hereby incorporated by reference in their entirety.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for inflammatory conditions, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the formula

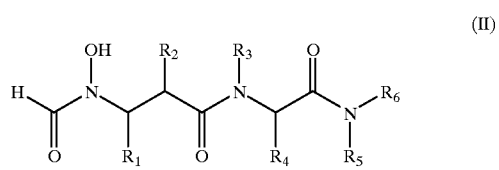

(II)

where

R$_1$ is

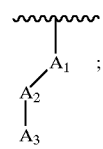

where

A$_1$ is alkylene, alkenylene, alkynylene, or a direct bond;

A$_2$ is O, S, SO, SO$_2$, or a direct bond;

A$_3$ is alkyl, alkenyl, alknyl, cycloalkyl, cycloalkenyl, heterocyclyl, heteroaryl, aryl, or hydrogen;

R$_2$ is

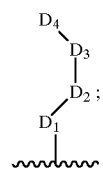

where

D₁ is

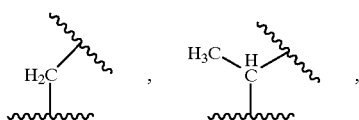

or a direct bond,

D₂ is alkylene, alkenylene, alkynylene, or a direct bond,

D₃ is cycloalkylene, cycloalkenylene, heterocyclylene, arylene, hetereroarylene, or a direct bond, D₄ is alkyl, aryl, heteroaryl, or hydrogen;

R₃ is hydrogen or lower alkyl;

R₄ is

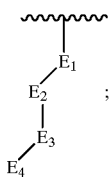

where

E₁ is alkylene, alkenylene, alkynylene, or a direct bond,

E₂ is S, O, SO, SO₂, C(O)O, OC(O), NR₇, C(O)NR₇, NR₇C(O), SO₂NR₇, or a direct bond, where R₇ is as defined;

E₃ is alkylene, cycloalkylene, cycloalkenylene, arylene, heterocyclylene, heteroarylene, or a direct bond;

E₄ is

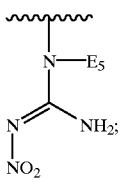

E₅ is lower alkyl or hydrogen;

R₅ is hydrogen or lower alkyl;

R₆ is

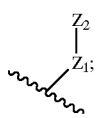

where

Z₁ is heteroarylene or a direct bond;

Z₂ is alkyl, alkenyl, alkynyl, cycloalkyl, cycloalkenyl, heterocyclyl, heteroaryl, aryl, NR₈R₉, OR₈, or hydrogen, where R₈ and R₉ are as defined; and R₇, R₈, and R₉ are, independently, hydrogen, alkyl, alkynyl, alkenyl, cycloalkyl, cycloalkenyl, aryl, heterocyclyl, or heteroaryl;

or a pharmaceutically acceptable salt, solvate, biohydrolyzable ester, biohydrolyzable amide, affinity reagent, or prodrug thereof.

2. A compound of the formula:

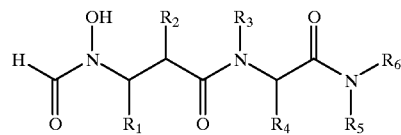

(II)

where

R₁ is methyl, trifluoromethyl, ethyl, phenylsulfanylmethyl, phenylsulfonylmethyl, thiophene-2-sulfanylmethyl, thiophene-2-sulfonylmethyl, isopropyl, 3-methyl-1-butyl, benzyloxymethyl, 2-benzyloxy-1-ethyl, benzyl, n-propyl, 3,3,3-trifluoro-1-propyl, or cyclopropyl;

R₂ is isobutyl, cyclohexylmethyl, 3-(2-furyl)-1-propyl, 3-(4-biphenyl)-1-propyl, 4-methylcyclohexylmethyl, cycloheptymethyl, cyclohexyl, 5-methylthiophene-2-methyl, 4-phenyl-1-butyl, 3-phenyl-1-propyl, or benzyl;

R₃ is hydrogen, methyl, or ethyl;

R₄ is 3-(nitroimino-amino)methylamino-1-propyl, 3-(nitroimino-amino)methyl-ethylamino-1-propyl, 3-(nitroimino-amino)methyl-methylamino-1-propyl, 3-(nitroimino-amino)methyl-isopropylamino-1-propyl, 2-(nitroimino-amino)methylamino-1-ethylaminocarbonylethyl, 2-(nitroimino-amino)methylamino-1-ethylaminocarbonylmethyl, 4-(nitroimino-amino)methylamino-1-butyl, or 4-(nitroimino-amino)methylamino-2-butyl;

R₅ is hydrogen, methyl, ethyl, or n-propyl; and

R₆ is hydrogen, methyl, 5-ethyl-2-thiazolyl, cyclopropyl, cyclobutyl, cycloheptyl, 2,2,2-trifluoroethyl, cyclopentyl, 3-cyclopenten-1-yl, 2-pyridyl, 1,3,4-thiadiazol-2-yl, or 2-thiazolyl.

3. A compound of the formula:

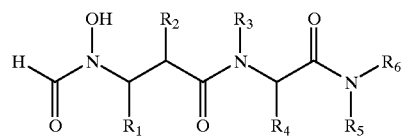

(II)

where

R is methyl, isopropyl, benzyl, n-propyl, 3,3,3-trifluoro-1-propyl, or cyclopropyl;

R₂ is isobutyl, cyclohexylmethyl, 4-methylcyclohexylmethyl, 5-methylthiophene-2-methyl, 3-phenyl-1-propyl, or benzyl;

R₃ is hydrogen;

R₄ is 3-(nitroimino-amino)methylamino-1-propyl, or 4-(nitroimino-amino)methylamino-2-butyl;

R₅ is hydrogen; and

R₆ is hydrogen, methyl, or 2-thiazolyl.

4. A compound of the formula:

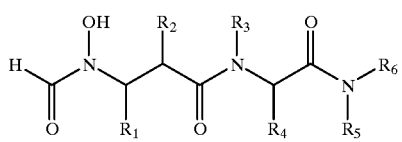

where
R$_1$ is methyl, n-propyl, or 3,3,3-trifluoro-1-propyl;
R$_2$ is isobutyl, 3-phenyl-1-propyl, or benzyl;
R$_3$ is hydrogen;
R$_4$ is 3-(nitroimino-amino)methylamino-1-propyl;
R$_5$ is hydrogen; and
R$_6$ is hydrogen, methyl, or 2-thiazolyl.

5. A compound of claim 1, wherein the compound is selected from the group consisting of (2R,3S)-3-(Formyl-hydroxyamino)-2-(2-methyl-1-propyl)hexanoic Acid [(1S)-4-(nitroimino-amino)methylamino-1-(1,3-thiazol-2-ylcarbamoyl)-1-butyl]amide; (2R,3S)-3-(Formyl-hydroxyamino)-2-(cyclohexylmethyl) hexanoic Acid [(1S)-4-(nitroimino-amino)methylamino-1-(1,3-thiazol-2-ylcarbamoyl)-1-butyl]amide; (2R,3S)-3-(Formyl-hydroxyamino)-2-(2-methyl-1-propyl)butanoic Acid [(1S,2R)-2-Methyl-4-(nitroimino-amino)methylamino-1-(1,3-thiazol-2-ylcarbamoyl)-1-butyl]amide; (2R,3S)-3-(Formyl-hydroxyamino)-2-(2-methyl-1-propyl)hexanoic Acid [(1S,2R)-2-Methyl-4-(nitroimino-amino)methylamino-1-(1,3-thiazol-2-ylcarbamoyl)-1-butyl]amide; (2R,3S)-3-(Formyl-hydroxyamino)-2-(2-methyl-1-propyl)-4-phenylbutanoic Acid [(1S)-4-(nitroimino-amino)methylamino-1-(1,3-thiazol-2-ylcarbamoyl)-1-butyl]amide; 2R,3S)-3-(Formyl-hydroxyamino)-2-(cyclohexylmethyl)-6,6,6-trifluorohexanoic Acid [(1S)-4-(nitroimino-amino)methylamino-1-(1,3-thiazol-2-ylcarbamoyl)-1-butyl]amide; (2R,3S)-3-(Formyl-hydroxyamino)-2-(4-methylcyclohexylmethyl)hexanoic Acid [(1S)-4-(nitroimino-amino)methylamino-1-(1,3-thiazol-2-ylcarbamoyl)-1-butyl]amide; (2R,3S)-3-(Formyl-hydroxy mino)-2-(4-methylcyclohexylmethyl)-4-methylpentanoic Acid [(1S)-4-(nitroimino-amino)methylamino-1-(1,3-thiazol-2-ylcarbamoyl)-1-butyl]amide; (2R,3S)-3-(Formyl-hydroxyamino)-2-(5-methyl-2-thiophenemethy)hexanoic Acid [(1S)-4-((nitroimino-amino)methylamino)-1-(1,3-thiazol-2-ylcarbamoyl)-1-butyl]amide; (2R,3S)-3-(Formyl-hydroxyamino)-2-(cyclohexylmethyl)-3-cyclopropylpropanoic Acid [(1S)-4-(nitroimino-amino)methylamino-1-(1,3-thiazol-2-ylcarbamoyl)-1-butyl]amide; (2R,3S)-3-(Formyl-hydroxyamino)-2-benzylhexanoic Acid [(1S)-4-(nitroimino-amino)methylamino-1-(1,3-thiazol-2-ylcarbamoyl)-1-butyllamide; (2R,3S)-3-(Formyl-hydroxyamino)-2-benzylhexanoic Acid [(1S)-4-(nitroimino-amino)methylamino-1-methylcarbamoyl-1-butyl]amide; (2R,3S)-3-(Formyl-hydroxyamino)-2-benzylhexanoic Acid [(1S)-4-(nitroimino-amino)methylamino-1-carbamoyl-1-butyl]amide; (2R,3S)-3-(Formyl-hydroxyamino)-2-(3-phenyl-1-propyl)butanoic Acid [(1S)-4-(nitroimino-amino)methylamino-1-methylcarbamoyl-1-butyl]amide; (2R,3S)-3-(Formyl-hydroxy amino)-2-(3-phenyl-1-propyl)butanoic Acid [(1S)-4-(nitroimino-amino)methylamino-1-(1,3-thiazol-2-ylcarbamoyl)-1-butyl]amide; (2R,3S)-3-(Formyl-hydroxyamino)-2-(4-methylcyclohexylmethyl)-6,6,6-trifluorohexanoic Acid [(1S)-4-(nitroimino-amino)methylamino-1-(1,3-thiazol-2-ylcarbamoyl)-1-butyl]amide; 2R,3S)-3-(Formyl-hydroxyamino)-2-(3-phenyl-1-propyl)-6,6,6-trifluorohexanoic Acid [(1S)-4-(nitroimino-amino)methylamino-1-(1,3-thiazol-2-ylcarbamoyl)-1-butyl]amide; (2R,3S)-3-(Formyl-hydroxyamino)-2-(3-phenyl-1-propyl)-6,6,6-trifluorohexanoic Acid (1S)-4-(nitroimino-amino)methylamino-1-carbamoyl-1-butyl]amide; (2R,3S)-3-(Formyl-hydroxyamino)-2-(3-phenyl-1-propyl)-6,6,6-trifluorohexanoic Acid [(1S)-4-(nitroimino-amiino)methylamino-1-methylcarbamoyl-1-butyl]amide; (2R,3S)-3-(Formyl-hydroxyamino)-2-(2-methyl-1-propyl)-6,6,6-trifluorohexanoic Acid [(1S)-4-(nitroimino-amino)methylamino-1-(1,3-thiazol-2-ylcarbamoyl)-1-butyl]amide; (2R,3S)-3-(Formyl-hydroxyamino)-2-(2-methyl-1-propyl)-6,6,6-trifluorohexanoic Acid [(1S)-4-(nitroimino-amino)methylamino-1-carbamoyl-1-butyl]amide; and (2R,3S)-3-(Formyl-hydroxyamino)-2-(2-methyl-1-propyl)-6,6,6-trifluorohexanoic Acid [(1S)-4-(nitroimino-amino)methylamino-1-methylcarbamoyl-1-butyl]amide.

6. A pharmaceutical composition comprising a pharmaceutically acceptable carrier and a pharmacologically effective amount of a compound of claim 1.

7. A pharmaceutical composition comprising a pharmaceutically acceptable carrier and a pharmacologically effective amount of the compound of claim 1 sufficient to inhibit the cellular release of mature tumor necrosis factor alpha.

8. A pharmaceutical composition comprising a pharmaceutically acceptable carrier and a pharmacologically effective amount of the compound of claim 1 sufficient to inhibit a matrix metalloprotease.

9. A pharmaceutical composition comprising a pharmaceutically acceptable carrier and a pharmacologically effective amount of the compound of claim 1 sufficient to inhibit the shedding of cell surface protein ectodomains.

10. A pharmaceutical composition comprising a pharmaceutically acceptable carrier and a pharmacologically effective amount of the compound of claim 1 sufficient to inhibit CD23 proteolysis.

11. A pharmaceutical composition comprising a pharmaceutically acceptable carrier and a pharmacologically effective amount of the compound of claim 1, sufficient to inhibit the growth of tumor metastases.

12. A phan-naceutical composition comprising a pharmaceutically acceptable carrier and a pharmacologically effective amount of the compound of claim 1, sufficient to treat arthritis.

13. A pharmaceutical composition comprising a pharmaceutically acceptable carrier and a pharmacologically effective amount of the compound of claim 1, sufficient to treat diabetes.

14. A pharmaceutical composition comprising a pharmaceutically acceptable carrier and a pharmacologically effective amount of the compound of claim 1, sufficient to treat periodontal disease.

15. A method of inhibiting a matrix metalloprotease, comprising the step of administering to a mammal in need thereof a pharmacologically effective amount of a compound of claim 1.

16. A method of inhibiting the intracellular release of tumor necrosis factor alpha, comprising the step of administering to a mammal in need thereof a pharmacologically effective amount of a compound of claim 1.

17. A method of inhibition of shedding of cell surface protein ectodomains, comprising the step of administering to a mammal in need thereof a pharmacologically effective amount of a compound of claim 1.

18. A method of inhibition of CD23 proteolysis, comprising the step of administering to a mammal in need thereof a pharmacologically effective amount of a compound of claim 1.

19. A method of treating periodontal disease comprising of administering to a mammal in need thereof a pharmacologically effective amount of a compound of claim 1.

* * * * *

UNITED STATES PATENT AND TRADEMARK OFFICE
CERTIFICATE OF CORRECTION

PATENT NO. : 6,191,150 B1
DATED : February 20, 2001
INVENTOR(S) : Andrews, et al.

It is certified that error appears in the above-identified patent and that said Letters Patent is hereby corrected as shown below:

Claim 12, column 76,
Line 50, delete "phan-naceutical" and insert therefor -- pharmaceutical --.

Signed and Sealed this

Thirtieth Day of October, 2001

*Attest:*

*Attesting Officer*

NICHOLAS P. GODICI
*Acting Director of the United States Patent and Trademark Office*